US012758231B2

(12) United States Patent
Kawamura et al.

(10) Patent No.: US 12,758,231 B2
(45) Date of Patent: Oct. 13, 2026

(54) HEMOSTATIC DEVICE

(71) Applicant: TERUMO KABUSHIKI KAISHA, Tokyo (JP)

(72) Inventors: Tomoya Kawamura, Odawara (JP); Tatsuya Ouchi, Fujinomiya (JP); Shosei Yoshimoto, Tokyo (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 38 days.

(21) Appl. No.: 18/883,491

(22) Filed: Sep. 12, 2024

(65) Prior Publication Data

US 2025/0000517 A1 Jan. 2, 2025

Related U.S. Application Data

(63) Continuation of application No. PCT/JP2023/008991, filed on Mar. 9, 2023.

(30) Foreign Application Priority Data

Mar. 18, 2022 (JP) ................................ 2022-044660

(51) Int. Cl.
*A61B 17/132* (2006.01)
*A61B 17/00* (2006.01)
*A61B 17/135* (2006.01)

(52) U.S. Cl.
CPC ........ *A61B 17/1325* (2013.01); *A61B 17/135* (2013.01); *A61B 2017/00544* (2013.01);
(Continued)

(58) Field of Classification Search
CPC .............. A61B 17/1325; A61B 17/135; A61B 17/1327; A61B 17/132; A61B 17/1322;
(Continued)

(56) References Cited

U.S. PATENT DOCUMENTS

2019/0133602 A1* 5/2019 Kiemeneij ......... A61B 17/1325
2021/0145452 A1* 5/2021 Hioki ................. A61B 17/1325

FOREIGN PATENT DOCUMENTS

CN 112914670 A 6/2021
JP 2022029463 A 2/2022
(Continued)

OTHER PUBLICATIONS

International Search Report (PCT/ISA/210) with translation and Written Opinion (PCT/ISA/237) mailed May 16, 2023, by the Japan Patent Office as the International Searching Authority for International Application No. PCT/JP2023/008991. (11 pages).
(Continued)

*Primary Examiner* — Jocelin C Tanner
(74) *Attorney, Agent, or Firm* — BUCHANAN INGERSOLL & ROONEY PC

(57) ABSTRACT

A hemostatic device includes a main body including a support member disposed to overlap an inflatable member and made of a material harder than the inflatable member, the main body has a first region where the support member is located, and a second region located between the first region and each of a first band body, a second band body, and a third band body, the second region is made of a material having higher ductility than the support member, and a width of the second region located between the first region and the second band body and a width of the second region located between the first region and the third band body decrease from a distal side to a proximal side of the support member.

19 Claims, 22 Drawing Sheets

(52) U.S. Cl.
CPC ............... *A61B 2017/00557* (2013.01); *A61B 2017/00862* (2013.01)

(58) Field of Classification Search
CPC .......... A61B 2017/00544; A61B 2017/00557; A61B 2017/00862; A61B 2017/00907
USPC ........................................................ 606/203
See application file for complete search history.

(56) References Cited

FOREIGN PATENT DOCUMENTS

| | | | |
|---|---|---|---|
| JP | 2022035820 | A | 3/2022 |
| WO | 2020027122 | A1 | 2/2020 |

OTHER PUBLICATIONS

English language translation of the International Search Report (Form PCT/ISA/210) and the Written Opinion of the International Searching Authority (Form PCT/ISA/237) issued May 16, 2023, by the Japanese Patent Office in corresponding International Application No. PCT/JP2023/008991. (7 pages).

* cited by examiner

HEMOSTATIC DEVICE

CROSS-REFERENCES TO RELATED APPLICATIONS

This application is a continuation of International Patent Application No. PCT/JP2023/008991 filed on Mar. 9, 2023, which claims priority to Japanese Patent Application No. 2022-044660 filed on Mar. 18, 2022, the entire content of both of which is incorporated herein by reference.

TECHNOLOGICAL FIELD

The present invention generally relates to a hemostatic device.

BACKGROUND DISCUSSION

One known catheter procedure is a procedure in which various medical elongated bodies are introduced into a blood vessel through a puncture site formed by puncturing a blood vessel of a limb such as an arm or a hand of a patient to perform diagnosis or a therapy at a lesion site. For example, U.S. Patent Application Publication No. 2019/0133602 discloses a hemostatic device for stopping bleeding at a puncture site formed to enable access to a blood vessel (including a distal radial artery) running in the hand.

The hemostatic device disclosed in the above-noted U.S. patent application publication includes a pressing member that applies a compressive force to a puncture site formed on a hand of a patient (hereinafter, also simply referred to as the "puncture site"), a plurality of band bodies for securing the pressing member to the hand of the patient, and a support member that is made of a material harder than the pressing member and compresses the pressing member against the hand of the patient.

SUMMARY

When hemostasis is performed on the puncture site formed on the patient's limb, an operator such as a doctor (hereinafter, referred to as the "operator") disposes the pressing member and the support member at the puncture site. The hemostatic device can stop bleeding at the puncture site by applying the compressive force to the puncture site using the pressing member in a state where the pressing member and the support member are disposed at the puncture site.

In the above hemostatic device, each of the plurality of band bodies wrapped around the hand of the patient is directly connected to the support member made of the material harder than the pressing member. Therefore, when hemostasis is performed using the hemostatic device, the following problem arises.

A size of a limb such as a hand of a patient, irregularities of a body surface of the limb, and the like vary from a patient to a patient. Therefore, if each band body can be disposed according to a size of a limb of a patient, irregularities of a body surface of the limb, and the like at the time of causing a hemostatic device to be worn on the limb of the patient, the hemostatic device can be appropriately worn on the patient according to the size and shape of the limb, a position of a puncture site formed on the limb, and the like. In the above-described hemostatic device, each of the plurality of band bodies is directly connected to the support member, and thus, a movable range of each of the band bodies near a connection position between the support member and each of the band bodies is narrow. Therefore, the hemostatic device has a low degree of freedom in a position of wrapping each of the band bodies on the limb of the patient, and there is room for improvement in terms of convenience.

The hemostatic device disclosed here can be applied to various patients having different sizes and shapes of limbs and can be applied to hemostasis of puncture sites formed at different positions.

A hemostatic device according to one version disclosed here by way of example includes: a cover member configured to cover a puncture site formed on a patient; and a pressing member disposed on the cover member and configured to compress the puncture site, wherein the cover member includes a main body in which the pressing member is located, a first band body configured to be disposed between fingers of the patient and extends from the main body in a first direction, a second band body extending from the main body in a second direction different from the first direction, and a third band body facing the second band body across the pressing member and extending from the main body in a different direction from the first band body and the second band body, the main body includes a support member disposed to overlap the pressing member and made of a material harder than the pressing member, the main body has a first region where the support member is located, and a second region located between the first region and each of the first band body, the second band body, and the third band body, the second region is made of a material having higher ductility than the support member, and a width of the second region located between the first region and the second band body and a width of the second region located between the first region and the third band body decreasing from a distal side of the support member to a proximal side of the support member.

The main body of the hemostatic device includes the support member disposed so as to overlap the pressing member and made of the material harder than the pressing member. Furthermore, the main body has the first region where the support member is located, and the second region located between the first region and each of the first band body, the second band body, and the third band body. The second region is made of the material having higher ductility than the support member. Therefore, when each of the band bodies is pulled, the second region is configured to move in accordance with the pulling operation. It is possible to appropriately adjust a position where each of the band bodies is wrapped around a limb of the patient by pulling each of the band bodies to move the second region at the time of causing the hemostatic device to be worn on the patient. Therefore, the hemostatic device can be applied to various patients having different sizes and shapes of limbs, and can also be applied to hemostasis of puncture sites formed at different positions. Furthermore, in the hemostatic device, the width of the second region located between the first region and the second band body and the width of the second region located between the first region and the third band body decrease (narrow) from the distal side of the support member to the proximal side of the support member. Therefore, the hemostatic device can prevent the second region located on the proximal side of the support member from being excessively moved when the second band body and the third band body are wrapped around the limb of the patient. Therefore, the hemostatic device can prevent positions where the second band and the third band are wrapped around the limb of the patient from being shifted to the proximal side of the support member when the second band body and the third band body are wrapped around the limb of the patient. In the hemostatic device, the second band body and the third band body can be wrapped around the limb of the patient along directions of being separated from each other with the support member as a reference, the directions being substantially horizontal to each other. Therefore, the hemostatic device enables the second band body and the third band body to be more firmly wrapped around the limb of the patient. Therefore, the hemostatic device can improve a compressive force applied to the puncture site by the pressing member in a state where the hemostatic device is worn on the limb of the patient.

Another aspect involves a hemostatic device to be applied to a hand of a patient to stop bleeding at a puncture site on the patient's hand, wherein the hemostatic device comprises a pressing member configured to compress the puncture site on the hand of the patient, and a cover member configured to cover the puncture site on the patient's hand and positioned in overlying relation to the pressing member. The cover member includes a main body, a first band body configured to be disposed between fingers of the patient's hand, a second band body and a third band body, with the second and third band bodies being configured to be wrapped around the hand of the patient so that fasteners provided on the second and third band bodies engage one another to secure the second and third band bodies to each other in a wrapped state around the patient's hand. The main body has an outer periphery and includes a support member, a first layer and a second layer, with the first layer having an outer periphery and the support member also having an outer periphery. The support member is located between the first and second layers and overlies the pressing member, and the support member is made of a material different from the first and second layers, with the support member being harder than the pressing member, and the support member including one side and an oppositely facing other side. The first band body extends from the main body in a first direction, the second band body extends from the main body in a second direction different from the first direction, and the third band body extends from the main body in a third direction different from both the first direction and the second direction. The second band body has a center line and an end portion terminating at a free end, the third band body has a center line and an end portion terminating at a free end, and the center line of the second band body and the center line of the third band body intersecting one another in the support member as seen in a plan view of the hemostatic device. The outer periphery of the main body is located outwardly of the outer periphery of the first layer and the outer periphery of the support member in the plan view. The end portion of the second band body is fixed to the outer periphery of the main body so that the free end of the second band body faces the one side of the support member in the plan view, and a distance between the free end of the second band body and the one side of the support member in the plan view decreases in a direction away from the first band body. The end portion of the third band body is fixed to the outer periphery of the main body so that the free end of the third band body faces the other side of the support member in the plan view, and the distance between the free end of the third band body and the other side of the support member in the plan view decreases in a direction away from the first band body.

Another aspect involves a hemostatic device to be applied to a hand of a patient to stop bleeding at a puncture site on the patient's hand, wherein the hemostatic device comprises a pressing member configured to compress the puncture site on the hand of the patient, and a cover member configured to cover the puncture site on the patient's hand and positioned in overlying relation to the pressing member. The cover member includes a main body, a first band body configured to be disposed between fingers of the patient's hand, a second band body and a third band body, with the second and third band bodies being configured to be wrapped around the hand of the patient so that fasteners provided on the second and third band bodies engage one another to secure the second and third band bodies to each other in a wrapped state around the patient's hand. The main body includes a support member overlapping the pressing member and made of a material harder than the pressing member, and the main body also includes sheet material overlying the support member. The first band body has a center line and an end, the second band body has a center line and an end, and the third band body has a center line and an end, with the center line of the first band body intersecting the support member as seen in a plan view of the hemostatic device, and the center line of the second band body and the center line of the third band body intersecting one another in the support member as seen in the plan view of the hemostatic device. The end of the first band body is fixed to the outer periphery of the sheet material of the main body so that the end of the first band body and a first portion of the outer periphery of the sheet material are positioned in overlying relation to each other, the end of the second band body is fixed to the outer periphery of the sheet material of the main body so that the end of the second band body and a second portion of the outer periphery of the sheet material are positioned in overlying relation to each other, and the end of the third band body is fixed to the outer periphery of the sheet material of the main body so that the end of the third band body and a third portion of the outer periphery of the sheet material are positioned in overlying relation to each other. The second portion of the outer periphery of the sheet material and the third portion of the outer periphery of the sheet material are spaced outwardly away from an outer periphery of the support member as seen in the plan view. The hemostatic device is configured so that: i) the end of the second band body and the end of the third band body have a concavely curved end surface facing toward the support member; or ii) the end of the second band body that is positioned in overlying relation to the second portion of the outer periphery of the sheet material has a width less than a width of the second portion of the outer periphery of the sheet material, and the end of the third band body that is positioned in overlying relation to the third portion of the outer periphery of the sheet material has a width less than a width of the third portion of the outer periphery of the sheet material; or iii) the end of the second band body that is positioned in overlying relation to the second portion of the outer periphery of the sheet material has a width greater than a width of the second portion of the outer periphery of the sheet material, and the end of the third band body that is positioned in overlying relation to the third portion of the outer periphery of the sheet material has a width greater than a width of the third portion of the outer periphery of the sheet material; or iv) the end of the second band body is fused to the outer periphery of the sheet material of the main body at a plurality of second band body fused portions that are spaced apart from one another so that an unfused portion exists between immediately adjacent second band body fused portions, and the end of the third band body is fused to the outer periphery of the sheet material of the main body at a plurality of third band body fused portions that are spaced apart from one another so that an unfused portion exists between immediately adjacent third band body fused portions.

DETAILED DESCRIPTION

Hereinafter, embodiments of the hemostatic device disclosed here as examples of the new hemostatic device will be described with reference to the accompanying drawings. The following description does not limit the technical scope or the significance of each term disclosed in the claims. Furthermore, dimensional ratios of the drawings are exaggerated for illustration purpose and may differ from actual ratios.

Figure 23:
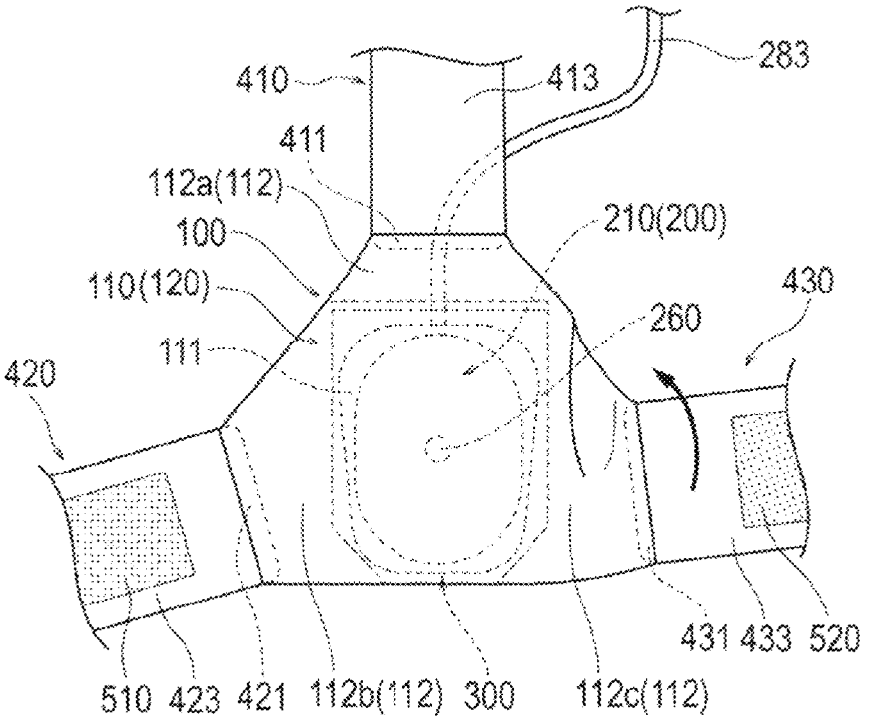
FIG. 23 is a plan view for describing an operational effect of the hemostatic device.
Figure 24:
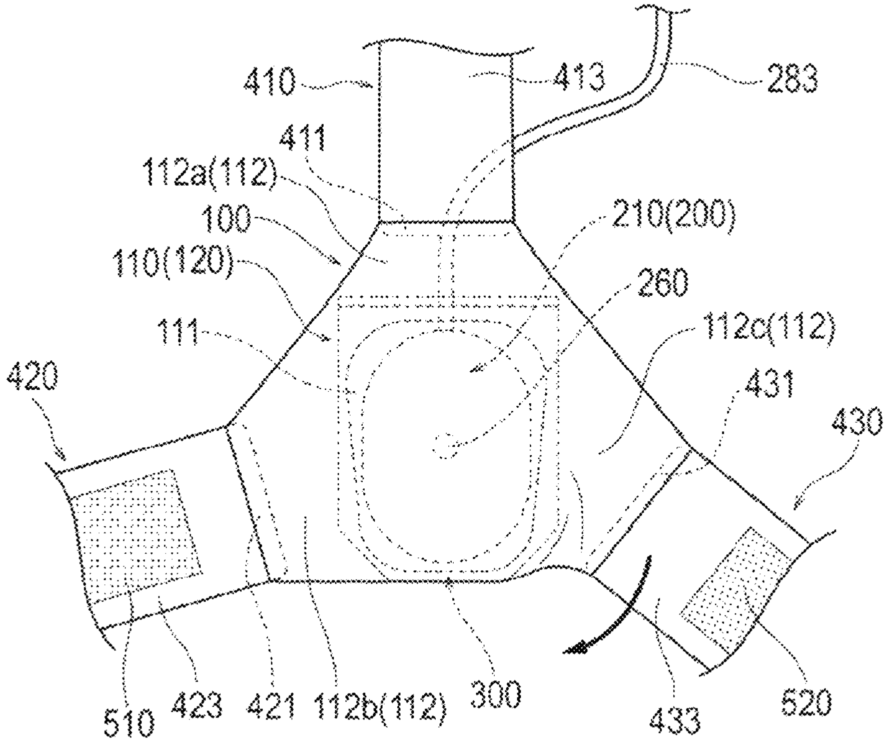
FIG. 24 is a plan view for describing the operational effect of the hemostatic device.

FIGS. 1 to 15 are views for describing a hemostatic device 10 according to the present embodiment. FIGS. 16 to 22 are views for describing a use example of the hemostatic device 10. FIGS. 23 and 24 are views for describing an operational effect of the hemostatic device 10.

For example, as illustrated in FIGS. 16, 19, 20, 21, and 22, the hemostatic device 10 can be used to stop bleeding at a first puncture site p1 (hereinafter, also referred to as a "first puncture site p1") formed in a hand H located on a distal side (fingertip side) of a forearm Ar of a patient when a sheath tube 610 of an introducer 600 placed at the first puncture site p1 is removed.

A specific position of the puncture site where bleeding is to be stopped by the hemostatic device 10 is not particularly limited, but the first puncture site p1 and a second puncture site p2 are exemplified in the present specification.

As illustrated in FIGS. 16, 19, 20, 21, and 22, the first puncture site p1 is a puncture site formed in a distal radial artery (hereinafter, also referred to as a "blood vessel V1") located on the distal side of a snuff box Sb of a palmar artery running on a dorsal side of a right hand H1 located on the distal side of the forearm Ar of the patient. Furthermore, the first puncture site p1 is located at a predetermined position avoiding a metacarpal bone B1 of an index finger and a metacarpal bone B2 of a thumb between the metacarpal bone B1 of the index finger and the metacarpal bone B2 of the thumb. The snuff box Sb is a cavity of the hand located near a radius when the patient spreads the thumb of the hand H.

Figure 16:
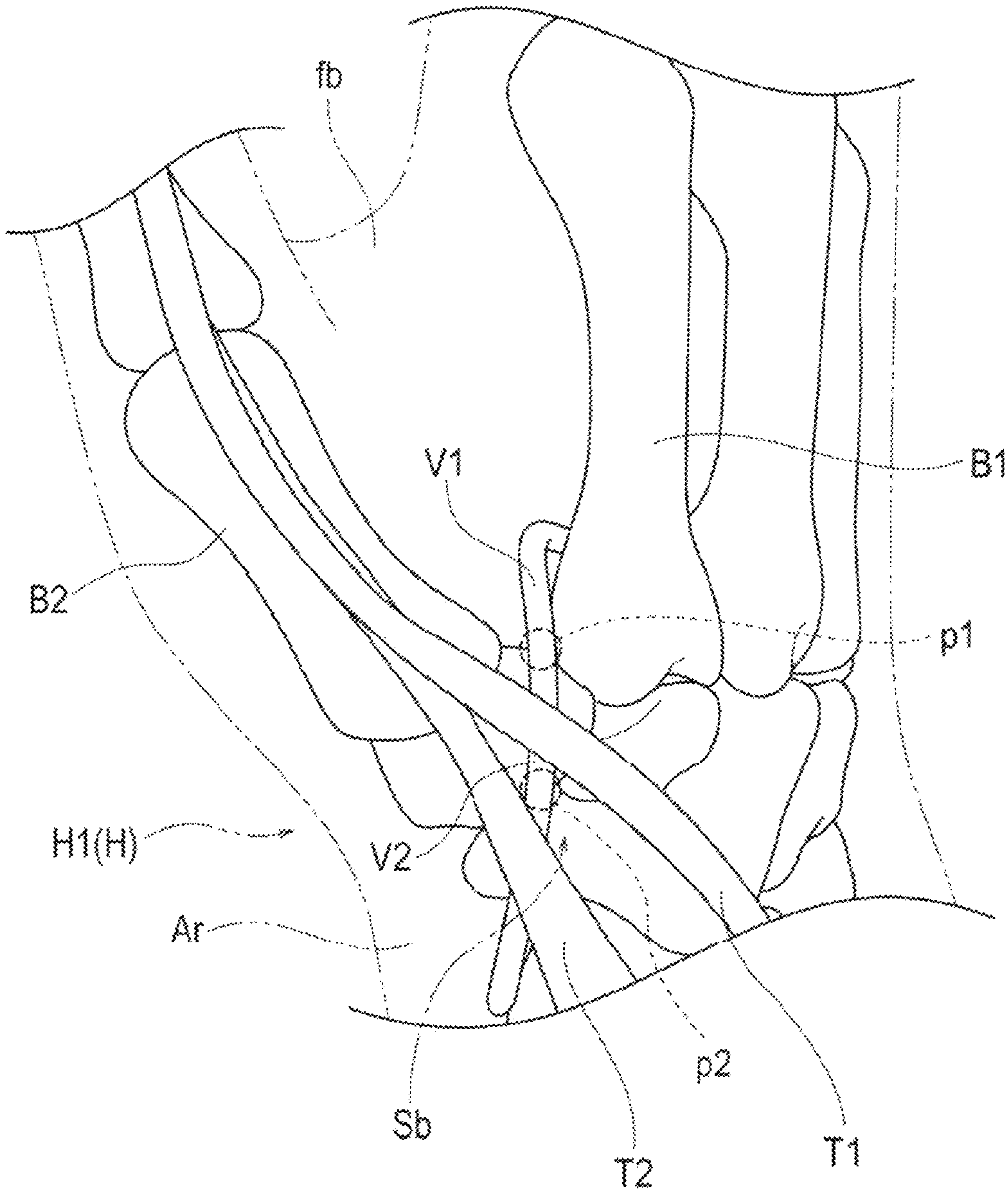
FIG. 16 is a view illustrating a hand (right hand) of a patient for which the hemostatic device is to be used.

As illustrated in FIG. 16, the second puncture site p2 is a puncture site formed in an artery V2 located in the snuff box Sb of the palmar artery running on the dorsal side of the right hand H1.

The second puncture site p2 is located on the forearm Ar side (proximal side) of the patient with respect to the first puncture site p1, and is located between an extensor pollicis longus muscle T1 and an extensor pollicis *brevis* muscle T2 located on the dorsal side of the right hand H1 of the patient. Furthermore, the second puncture site p2 is located at a predetermined position avoiding a position of the metacarpal bone B1 of the index finger and a position of the metacarpal bone B2 of the thumb.

The hemostatic device 10 can also be applied to hemostasis of a puncture site on a left hand of a patient formed at a position corresponding to the first puncture site p1 exemplified with the patient's right hand H1 or a puncture site on the left hand of the patient formed at a position corresponding to the second puncture site p2 exemplified with the patient's right hand H1.

Hereinafter, the hemostatic device 10 will be described in detail.

<Hemostatic Device>

As illustrated in FIGS. 1, 2, 16, 19, 20, and 21, the hemostatic device 10 generally includes a cover member 100 configured to cover the first puncture site p1 and a pressing member 200 disposed on the cover member 100 and configured to compress the first puncture site p1.

In the present specification, the fingertip side of a finger is defined as a "distal side", and the forearm Ar side is defined as a "proximal side" in a state where the hemostatic device 10 is worn on the right hand H1 of the patient. A "distal side" and a "proximal side" used in the description of the hemostatic device 10 are also defined similarly to directions defined above.

<Pressing Member>

The pressing member 200 can be formed of, for example, an inflatable member 210 configured to be inflatable by injection of a fluid. In the present embodiment, an example in which the pressing member 200 is formed of the inflatable member 210 will be described.

Figure 6:
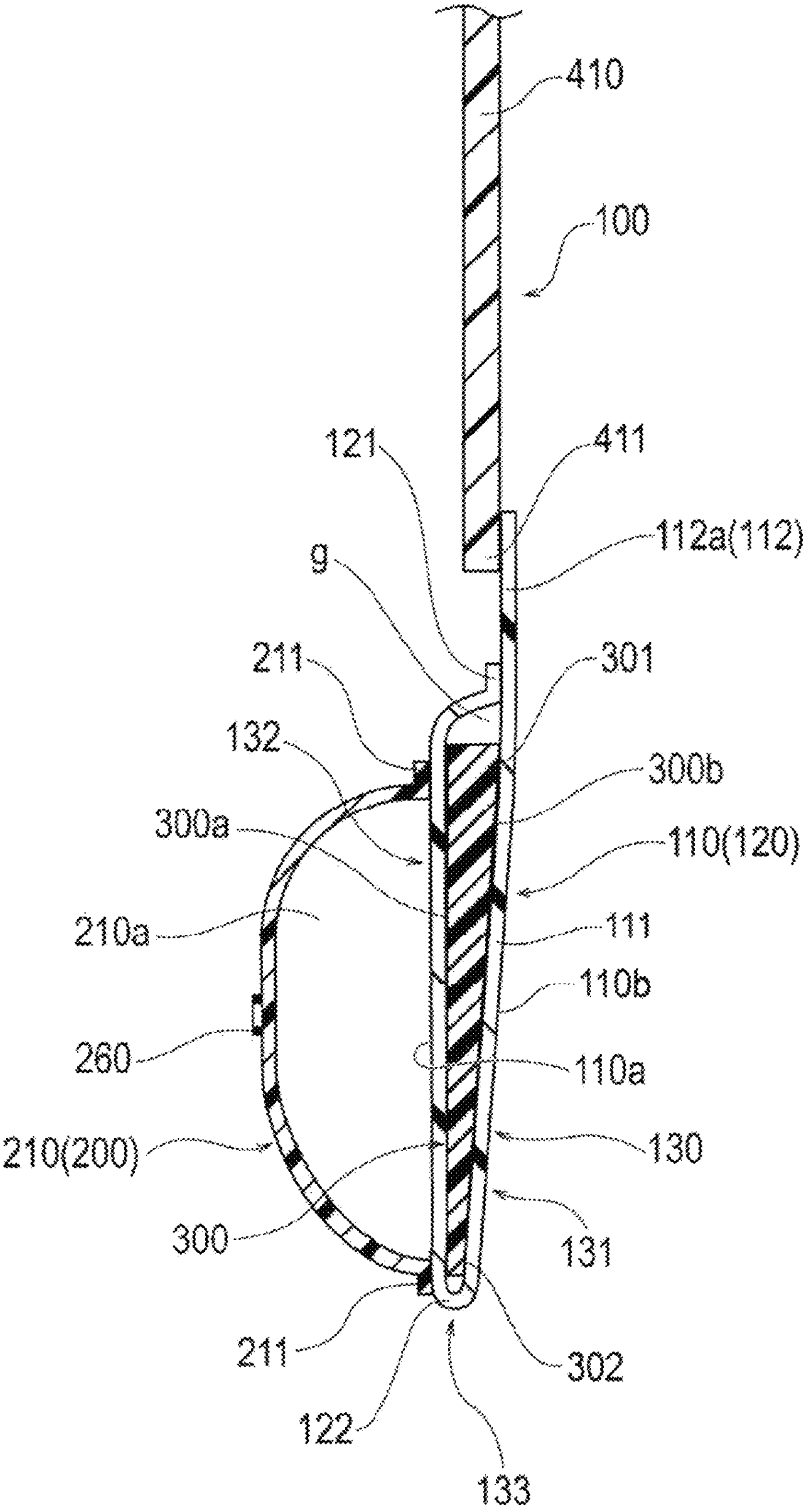
FIG. 6 is a partial cross-sectional view of the hemostatic device taken along an arrow 6-6 illustrated in FIG. 5, and is a view illustrating a state when an inflatable member inflates.
Figure 7:
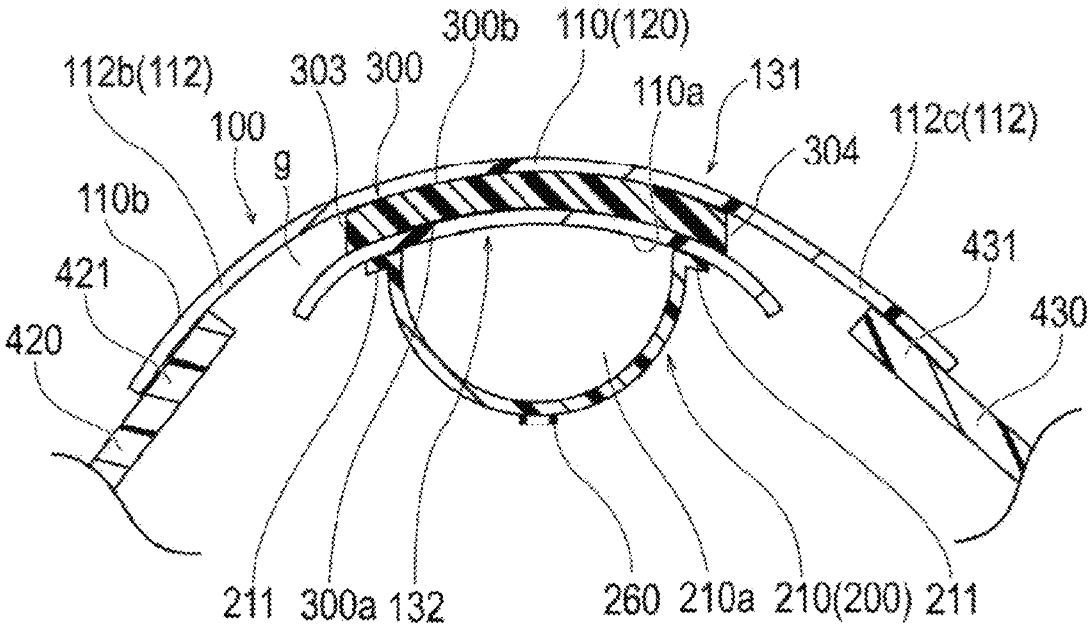
FIG. 7 is a partial cross-sectional view of the hemostatic device taken along an arrow 7-7 illustrated in FIG. 5, and is a view illustrating a state when the inflatable member inflates.

As illustrated in FIGS. 6 and 7, the inflatable member 210 includes an inner cavity 210*a* into which the fluid can be injected. The inflatable member 210 is configured to inflate as the fluid is injected into the inner cavity 210*a* and deflate as the fluid injected into the inner cavity 210*a* is discharged. The fluid used for the inflation of the inflatable member 210 is, for example, a gas such as air. FIGS. 6 and 7 illustrate cross-sectional views of the inflatable member 210 in an inflated state.

A tube 283 (see FIGS. 1 and 2) to be described later is coupled to the inner cavity 210*a* of the inflatable member 210.

As illustrated in FIGS. 6 and 7, the inflatable member 210 can be formed of, for example, a film-shaped member (sheet material) connected to a sheet material 120 forming a main body 110 of the cover member 100.

The inflatable member 210 can be disposed to form the inner cavity 210*a* against a lower surface region 132 of a retaining portion 130 formed by the sheet material 120.

An outer peripheral edge of the film-shaped member forming the inflatable member 210 forms an edge portion 211 of the inflatable member 210. The edge portion 211 of the inflatable member 210 can be connected to the sheet material 120 by, for example, fusing bonding, adhesion, or the like.

The film-shaped member forming the inflatable member 210 can be made of, for example, a resin material having a predetermined thickness.

A material of the film-shaped member forming the inflatable member 210 is not particularly limited, and for example, polyvinyl chloride, polyethylene, polypropylene, polybutadiene, polyolefins such as ethylene-vinyl acetate copolymer (EVA), polyesters such as polyethylene terephthalate (PET) and polybutylene terephthalate (PBT), various thermoplastic elastomers such as polyvinylidene chloride, silicone, polyurethane, polyamide elastomer, polyurethane elastomer, polyester elastomer, nylon, nylon elastomer, or any combination thereof (such as a blend resin, a polymer alloy and a laminate) can be used.

As illustrated in FIGS. 6 and 7, the inflatable member 210 is disposed on an inner surface 110*a* side of the main body 110 of the cover member 100.

Figure 20:
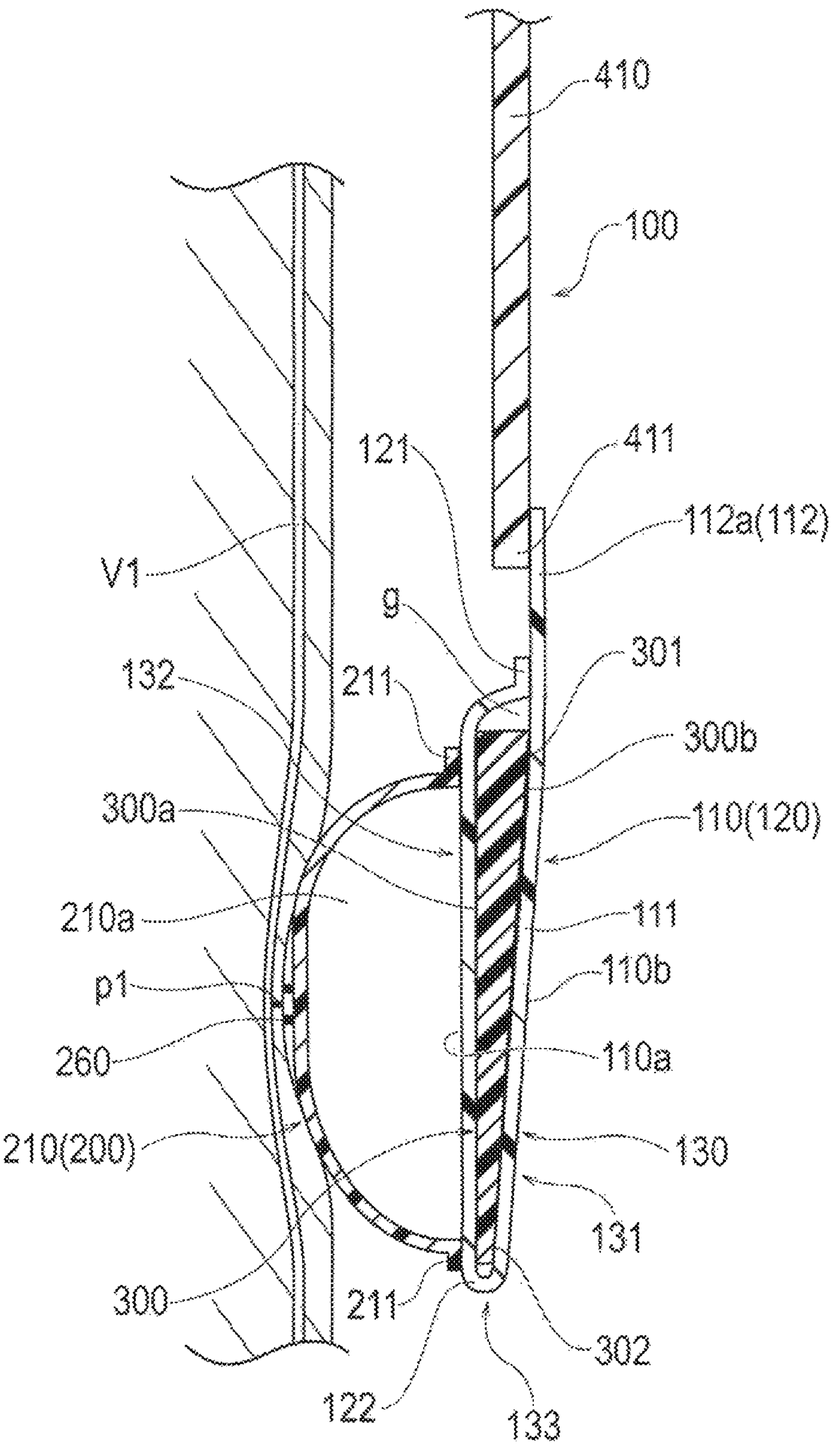
FIG. 20 is a partial cross-sectional view taken along an arrow 20-20 illustrated in FIG. 19.
Figure 21:
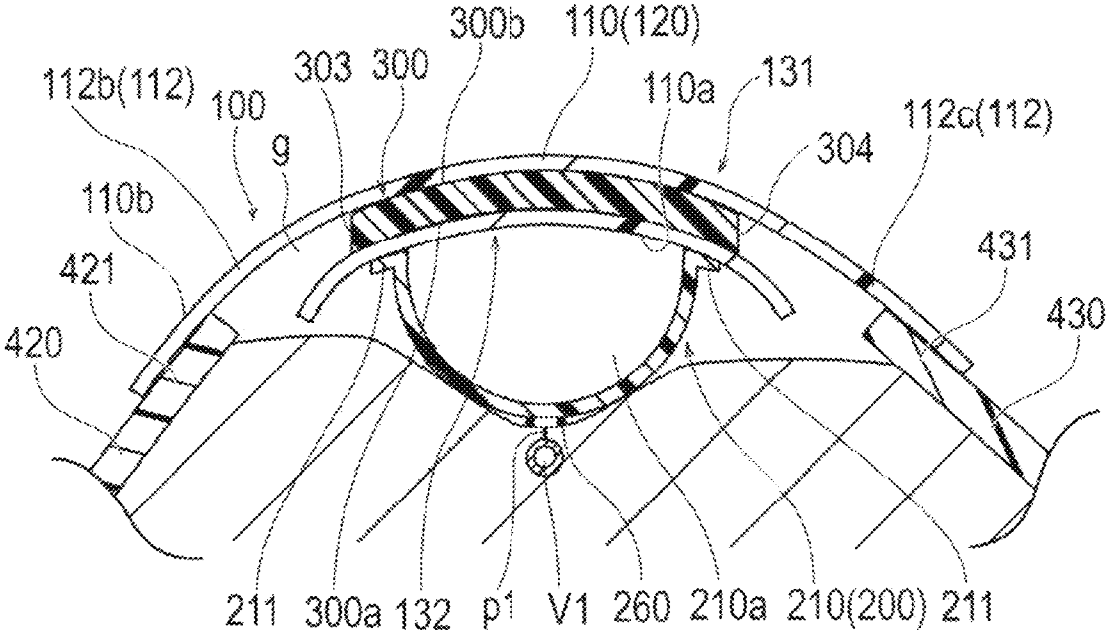
FIG. 21 is a partial cross-sectional view taken along an arrow 21-21 illustrated in FIG. 19.

In the present embodiment, the inner surface 110*a* of the main body 110 is formed of a surface disposed on a body surface side of the right hand H1 in the lower surface region 132 of the retaining portion 130 (see FIGS. 20 and 21). An outer surface 110*b* of the main body 110 is formed of a surface on a side facing the outside in an upper surface region 131 of the retaining portion 130.

Figure 8:
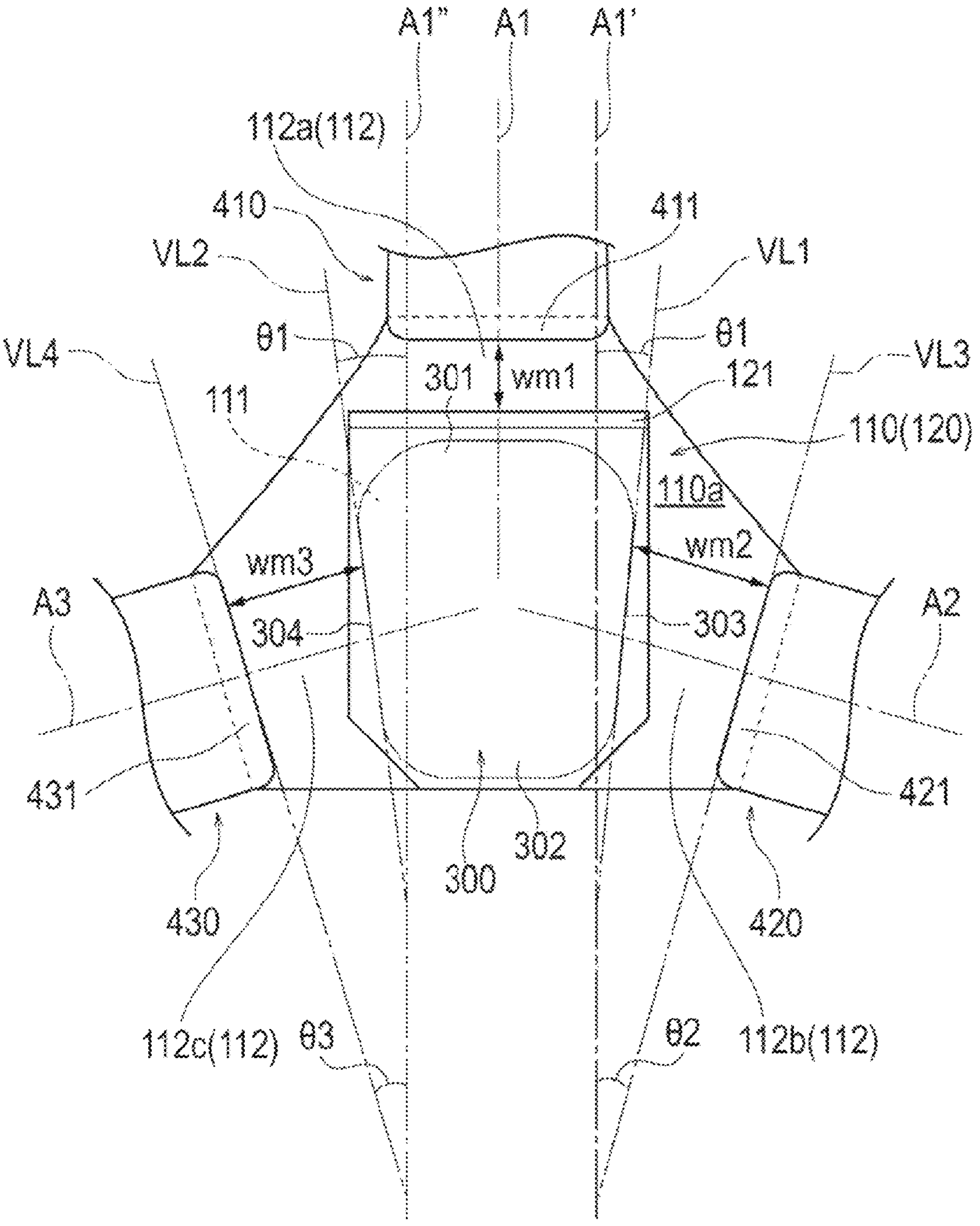
FIG. 8 is a view for describing a first region and a second region of the main body, and is a view briefly illustrating the inner surface side of the main body.
Figure 11:
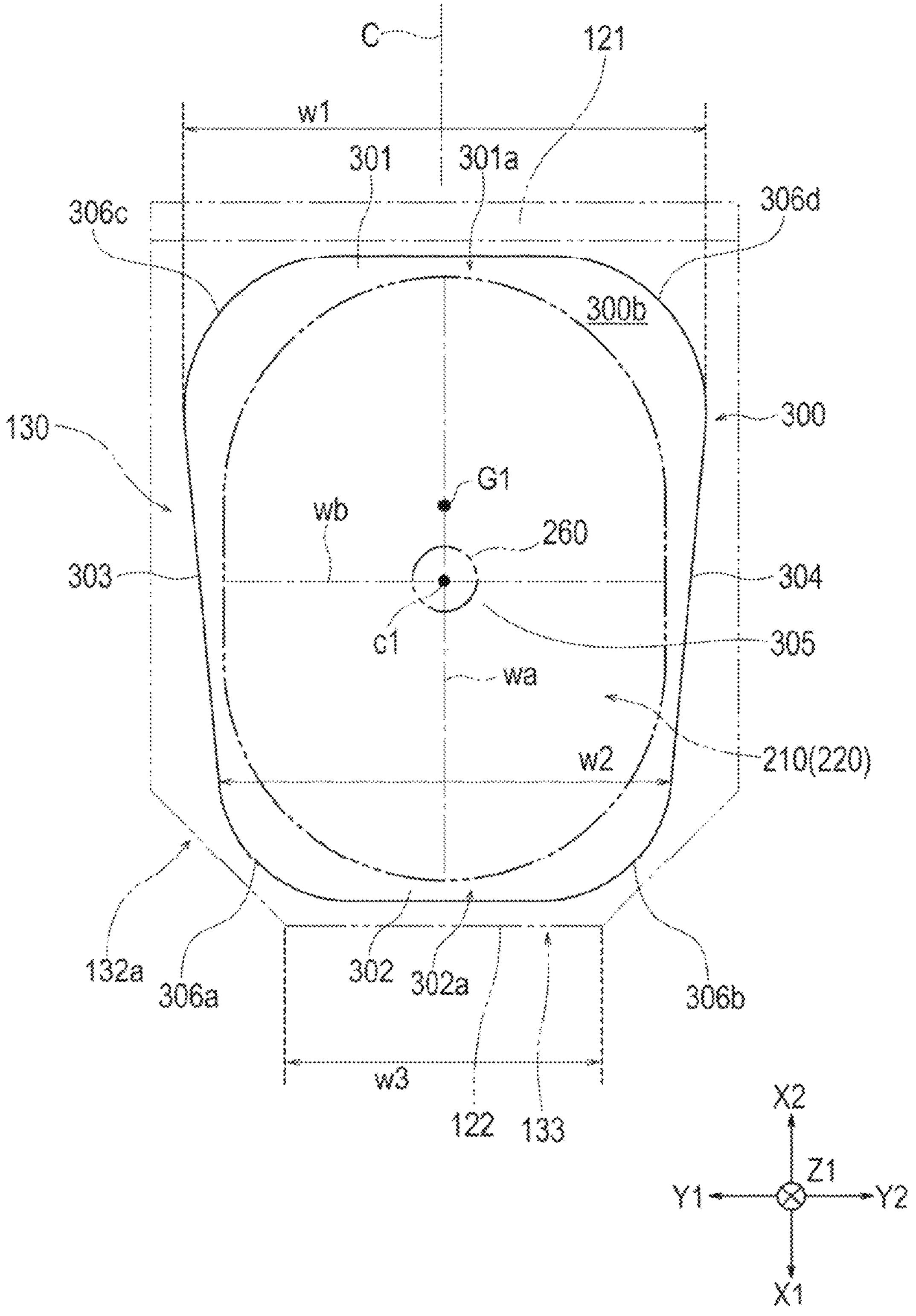
FIG. 11 is a plan view of a support member.

FIG. 11 is a plan view as seen from an outer surface 300*b* side of a support member 300. FIG. 8 illustrates a positional relationship among the inflatable member 210, the support member 300, and the retaining portion 130 in a deflated state. The inflatable member 210 and the retaining portion 130 are indicated by two-dot chain lines.

The inflatable member 210 has a longitudinal width wa passing through a center c1 of the inflatable member 210 and a lateral width wb that is orthogonal to the longitudinal width wa and passes through the center c1 of the inflatable member 210 in a state where the inflatable member 210 is deflated.

The center c1 of the inflatable member 210 is located at a center of an outer shape illustrated in the plan view of FIG. 11. In the present embodiment, the center c1 is located at a position where a center position of an axis (major axis) along the longitudinal width wa and a center position of an axis (minor axis) along the lateral width wb intersect. In the present embodiment, the center position of the axis (major axis) along the longitudinal width wa is a line segment passing through a point where distances from both ends of the axis along the longitudinal width wa are equal on the axis along the longitudinal width wa. Furthermore, the center position of the axis (minor axis) along the lateral width wb is a line segment passing through a point where distances from both ends of the axis along the lateral width wb are equal on the axis along the lateral width wb.

In the inflatable member 210, the lateral width wb is shorter than the longitudinal width wa. In the present embodiment, the inflatable member 210 has a substantially oval shape that is rotationally symmetric with respect to the center c1 in the plan view illustrated in FIG. 11.

Figure 17:
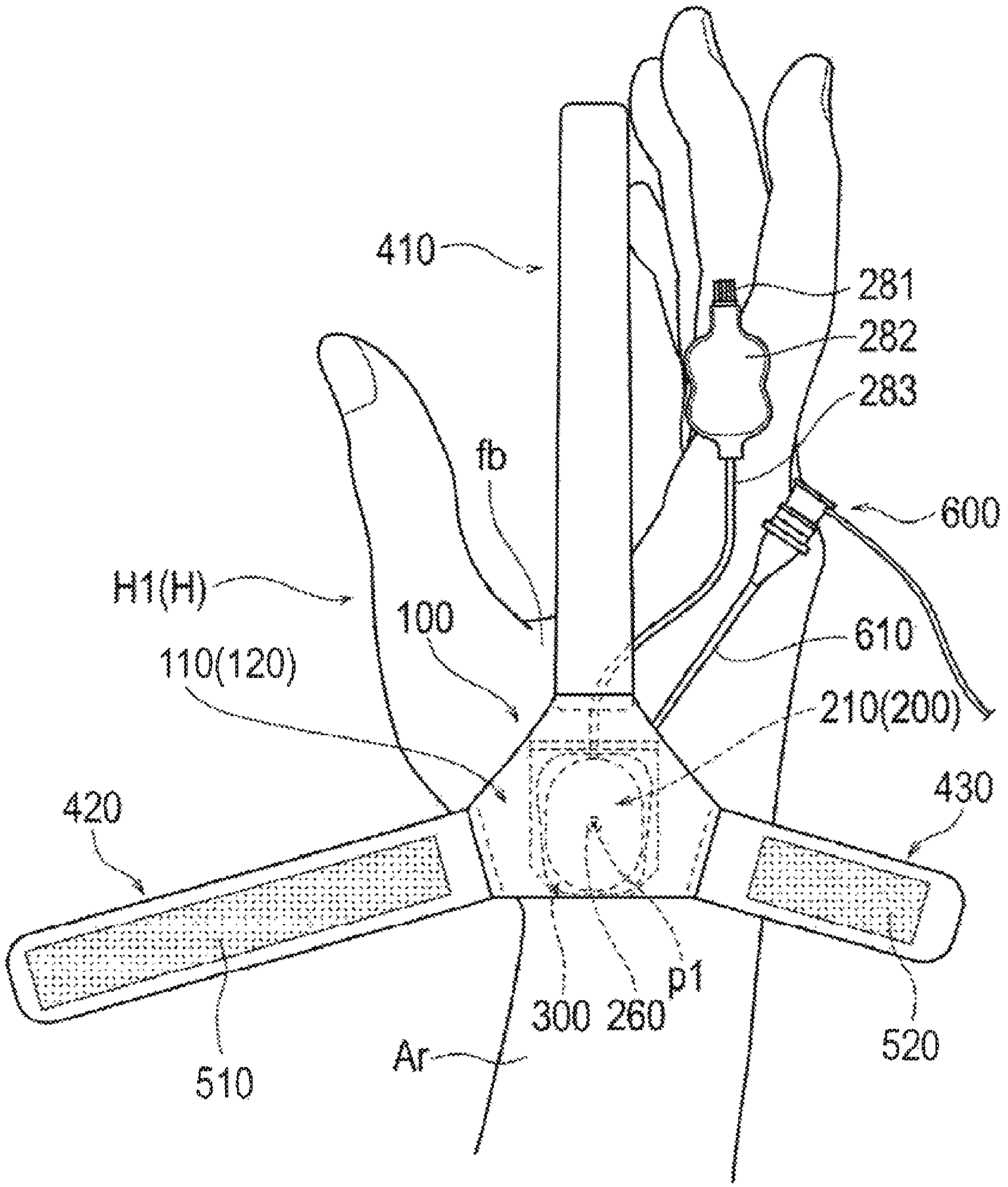
FIG. 17 is a view schematically illustrating a use example of the hemostatic device.
Figure 18:
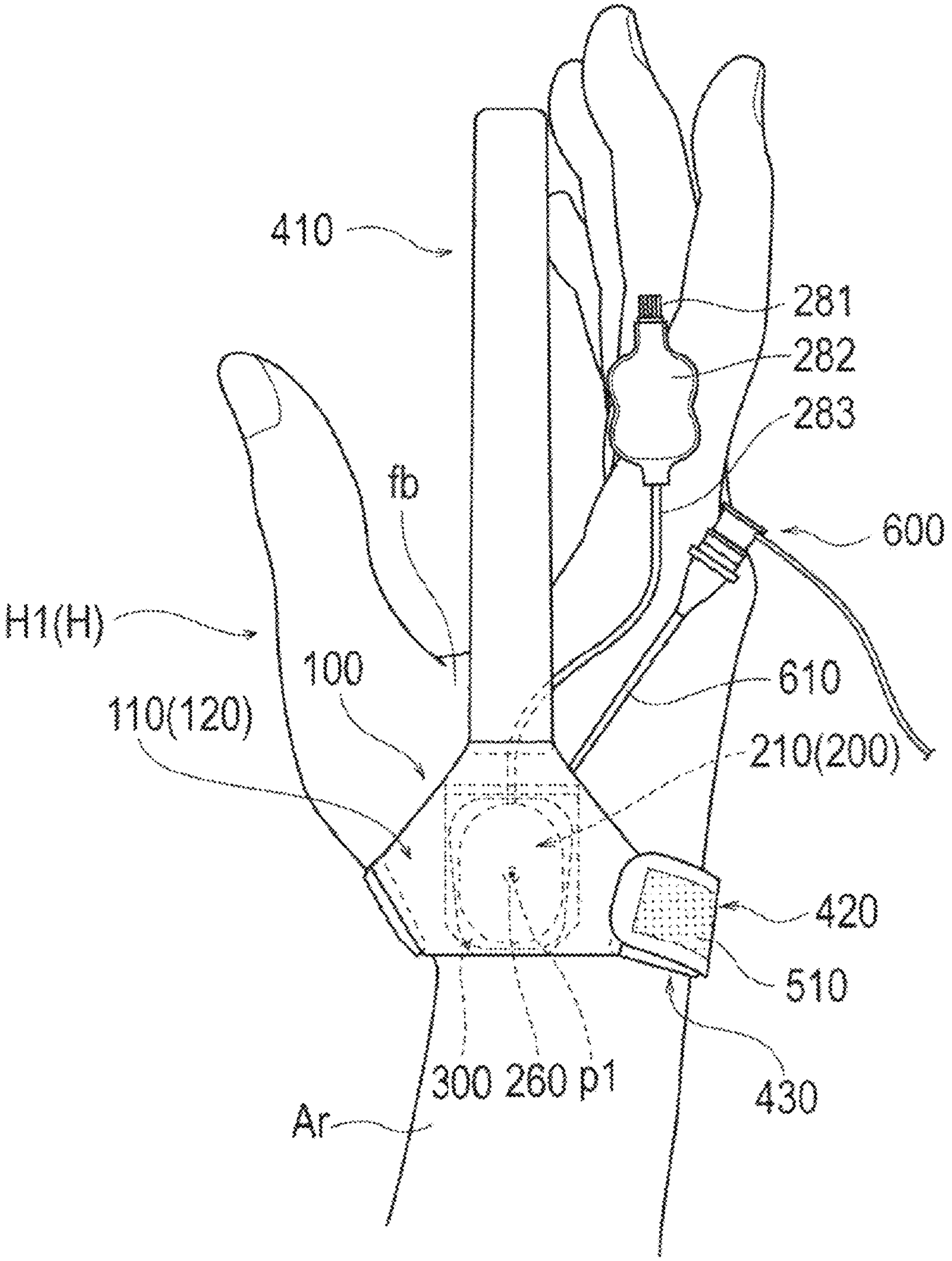
FIG. 18 is a view schematically illustrating the use example of the hemostatic device.
Figure 19:
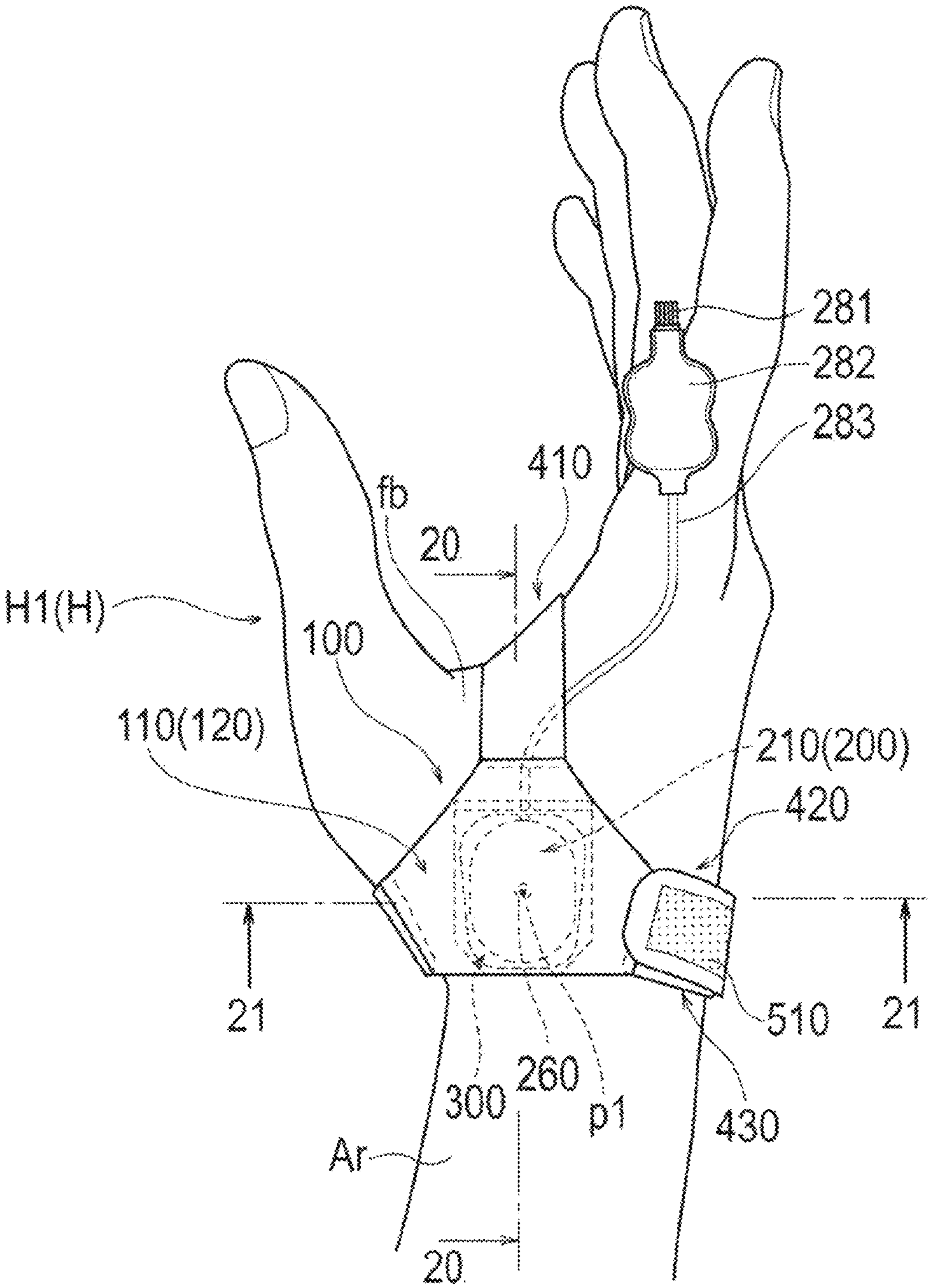
FIG. 19 is a view schematically illustrating the use example of the hemostatic device.

As illustrated in FIGS. 17, 18, and 19, the inflatable member 210 includes a marker portion 260 for aligning the inflatable member 210 with the first puncture site p1.

In the present embodiment, as illustrated in FIG. 11, the marker portion 260 is located at a position overlapping the center c1 of the inflatable member 210.

As illustrated in FIG. 11, the marker portion 260 is located on the proximal side of the main body 110 with respect to a center of gravity G1 of the support member 300.

Figure 4:
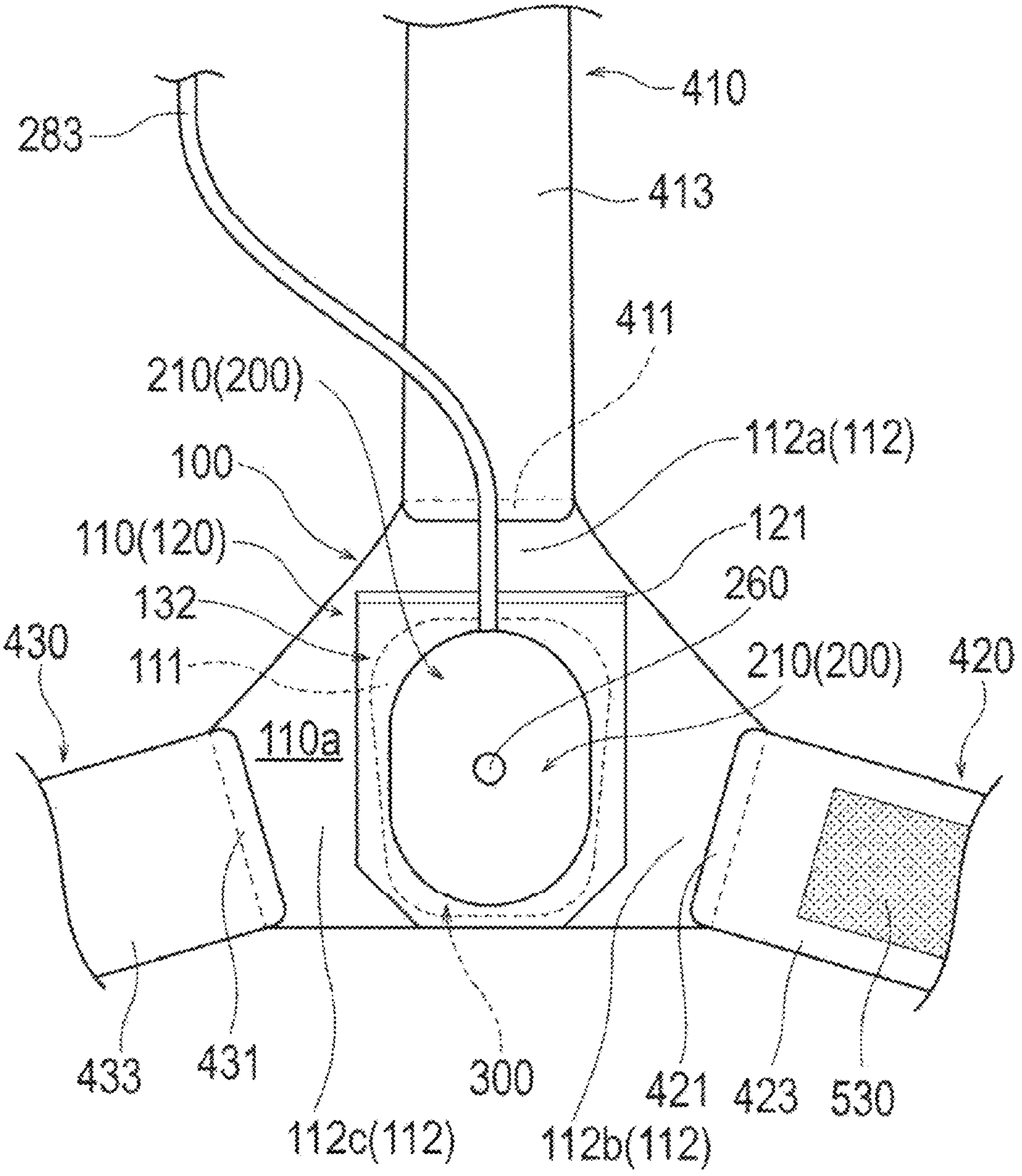
FIG. 4 is an enlarged view illustrating a part of the hemostatic device as seen from an inner surface side of the main body of the cover member.

As illustrated in FIGS. 4 and 11, the marker portion 260 can include a transparent central portion surrounding the center c1 and a colored circular frame portion surrounding the central portion.

As illustrated in FIGS. 6 and 7, the marker portion 260 is disposed on an outer surface of the inflatable member 210. The marker portion 260 may be disposed on an inner surface of the inflatable member 210 facing the inner cavity 210*a*.

A specific shape, color, formation method, or the like of the marker portion 260 is not particularly limited. The marker portion 260 can also include, for example, a circular marker configured entirely in color, a marker configured by a transparent central portion and a rectangular frame portion, a rectangular marker configured entirely in color, or the like.

The planar shape of the inflatable member 210 is not limited only to the oval shape. For example, the inflatable member 210 may have a planar shape such as a circle, an ellipse, or a rectangle. When the inflatable member 210 is configured to have the planar shape such as the circle, the ellipse, or the rectangle, the center c1 of the inflatable member 210 can be defined by the center position of the outer shape in the plan view.

A specific configuration of the inflatable member 210 is not particularly limited. For example, the inflatable member 210 may be formed by joining one sheet-like member with an edge portion of another sheet-like member in a state where the inner cavity 210*a* is formed between both the sheet-like members. In such a case, in the inflatable member 210, the surface of the one sheet-shaped member is connected to the sheet material 120 forming the main body 110 of the cover member 100. Furthermore, the inflatable member 210 can also be formed of, for example, one bag-shaped member shaped to include the inner cavity 210*a* inside. In such a case, in the inflatable member 210, a part of the surface of the bag-shaped member is connected to the sheet material 120 forming the main body 110 of the cover member 100.

<Cover Member>

Figure 5:
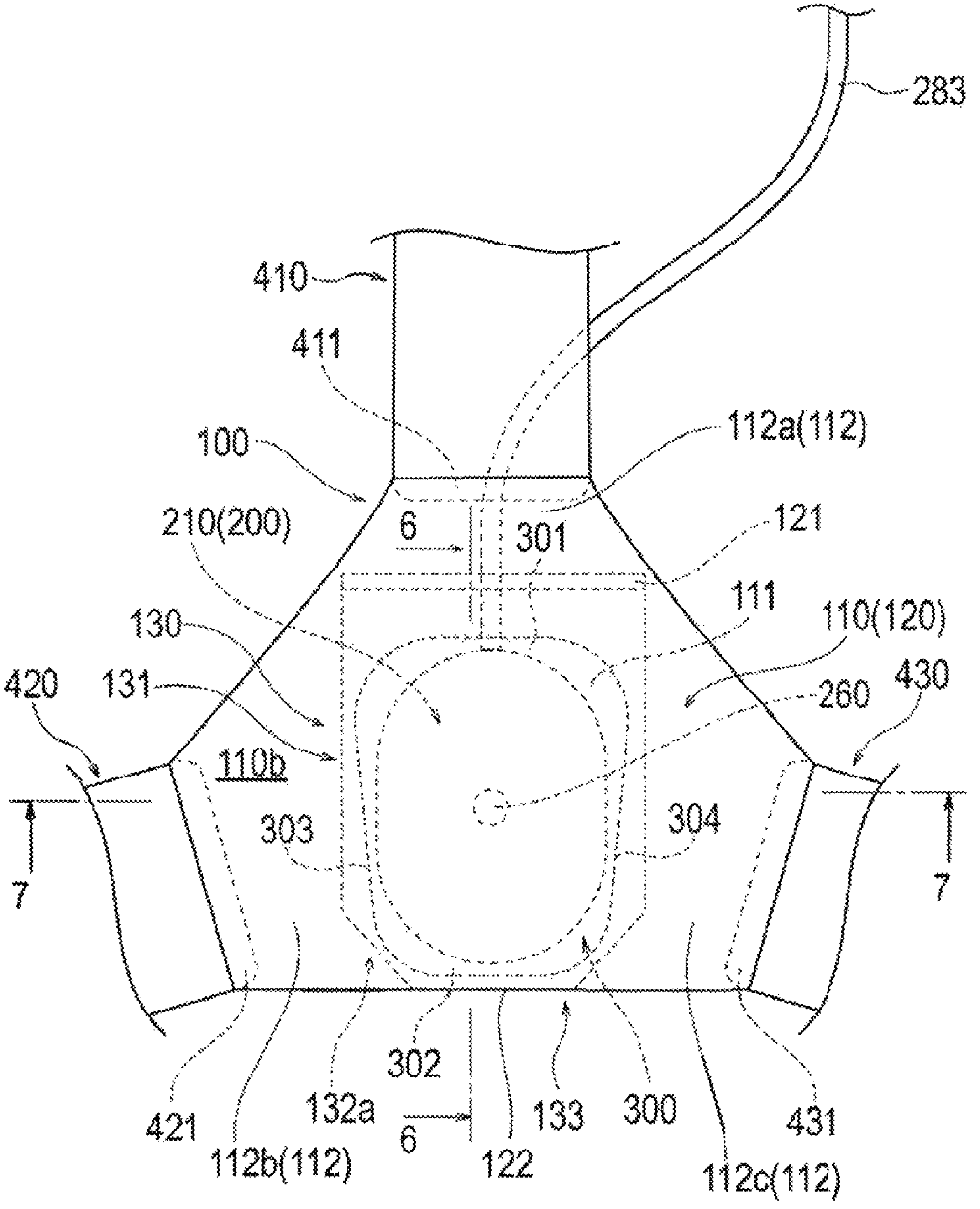
FIG. 5 is an enlarged view illustrating a part of the hemostatic device as seen from the outer surface side of the main body of the cover member.

As illustrated in FIGS. 5, 6, and 7, the cover member 100 includes the main body 110 in which the inflatable member 210 is located, a first band body 410 configured to be disposed between fingers of the patient and extends from the main body 110 in a first direction, a second band body 420 extending from the main body 110 in a second direction different from the first direction, and a third band body 430 facing the second band body 420 across the inflatable member 210 and extending from the main body 110 in a third direction different from the first direction and the second direction.

As illustrated in FIGS. 5, 6, and 7, the main body 110 includes the support member 300 formed of a material harder than the inflatable member 210. The support member 300 is configured to overlap the inflatable member 210 in the plan views illustrated in FIGS. 4 and 5.

As illustrated in FIGS. 6 and 7, the main body 110 includes the retaining portion 130 that has a two-layer structure and retains the support member 300.

The retaining portion 130 includes an upper surface region 131 located on the outer surface 300*b* side of the support member 300, a lower surface region 132 that is located on the inner surface 300*a* side of the support member 300 and faces the upper surface region 131 across the support member 300, and a curved region 133 connecting the upper surface region 131 and the lower surface region 132 on the proximal side of the support member 300 (a lower end 302 side of the support member 300).

The curved region 133 is formed by folding a part of the main body 110 toward the first band body 410 side. In the present embodiment, the retaining portion 130 having an insertion portion g into which the support member 300 can be inserted is formed in the main body 110 by folding a part of the sheet material 120 forming the main body 110 from the proximal side to the distal side.

As illustrated in FIGS. 5 and 6, a first end 121 located on the distal side of the folded part of the sheet material 120 is connected to the sheet material 120 at a position on the distal side of an upper end 301 of the support member 300. The first end 121 forms a distal portion of the retaining portion 130.

As illustrated in FIGS. 6 and 8, a proximal portion 122 of the cover member 100, formed of a part of the sheet material 120, is located in the curved region 133.

As illustrated in FIG. 6, in the retaining portion 130, the insertion portion g is closed between the first end 121 and the curved region 133 in a direction of the longitudinal width wa (see FIG. 11) of the inflatable member 210. Furthermore, as illustrated in FIG. 7, in the retaining portion 130, the insertion portion g communicates with the outside on the second band body 420 side and the third band body 430 side in a direction of the lateral width wb (see FIG. 11) of the inflatable member 210.

As illustrated in FIGS. 1, 2, 4, and 5, the first band body 410 includes one end 411 connected to the main body 110 of the cover member 100, the other end 412 located opposite to the one end 411, and a main body 413 extending between the one end 411 and the other end 412.

Figure 22:
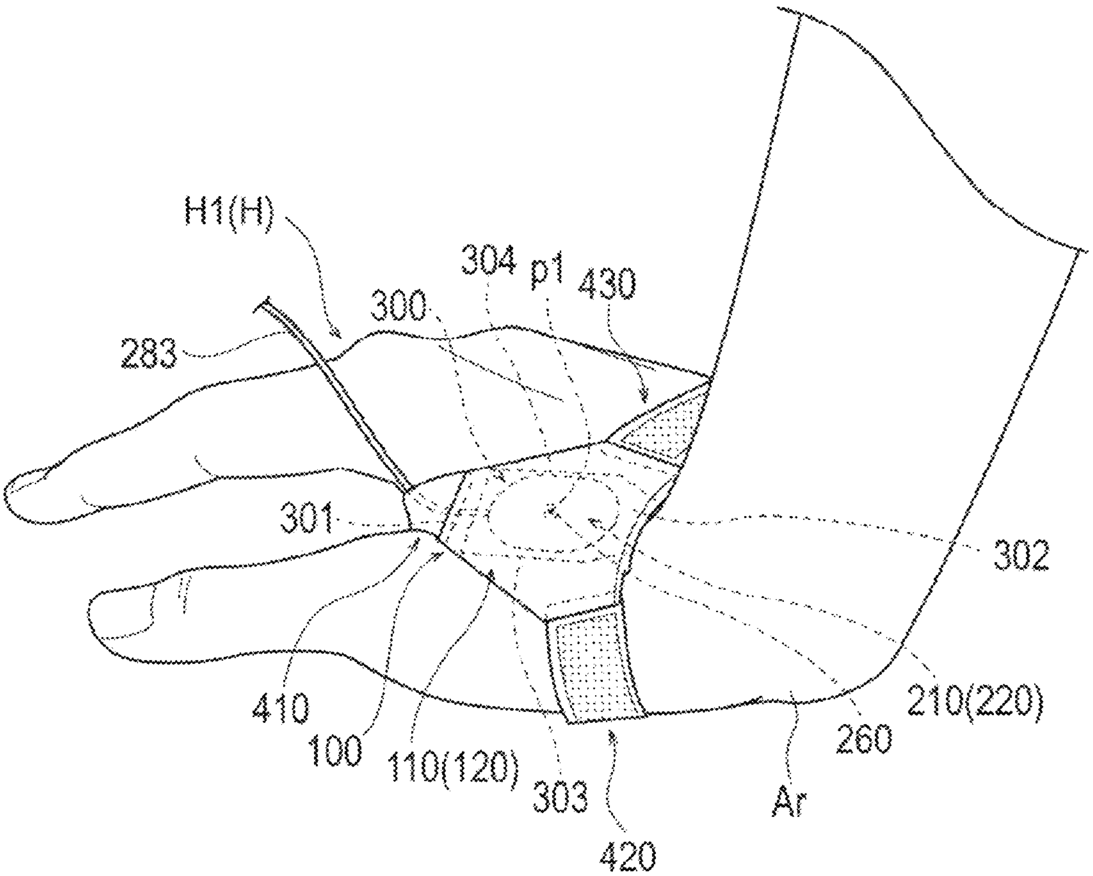
FIG. 22 is a view illustrating the right hand of the patient wearing the hemostatic device.

As illustrated in FIGS. 19 and 22, the first band body 410 can be disposed so as to be hooked on an interdigital part fb located between the thumb and the index finger of the right hand H1 of the patient in a state where the inflatable member 210 is disposed at the first puncture site p1.

As illustrated in FIGS. 1, 2, 4, and 5, the second band body 420 includes one end 421 connected to the main body 110 of the cover member 100, the other end 422 located opposite to the one end 421, and a main body 423 extending between the one end 421 and the other end 422.

As illustrated in FIGS. 1, 2, 4, and 5, the third band body 430 includes one end 431 connected to the main body 110 of the cover member 100, the other end 432 located opposite to the one end 431, and a main body 433 extending between the one end 431 and the other end 432.

As illustrated in FIGS. 19 and 22, the second band body 420 and the third band body 430 can be disposed so as to be wrapped along the outer periphery of the right hand H1 when the hemostatic device 10 is worn on the right hand H1 of the patient.

The second band body 420 and the third band body 430 are located at positions facing each other with the inflatable member 210 interposed therebetween in the plan view illustrated in FIG. 5. Therefore, when the second band body 420 and the third band body 430 are wrapped around the right hand H1, a tensile force in a direction of separating the second band body 420 and the third band body 430 from each other is applied to both, and a tensile force in the same direction is also applied to the main body 110.

Figure 9:
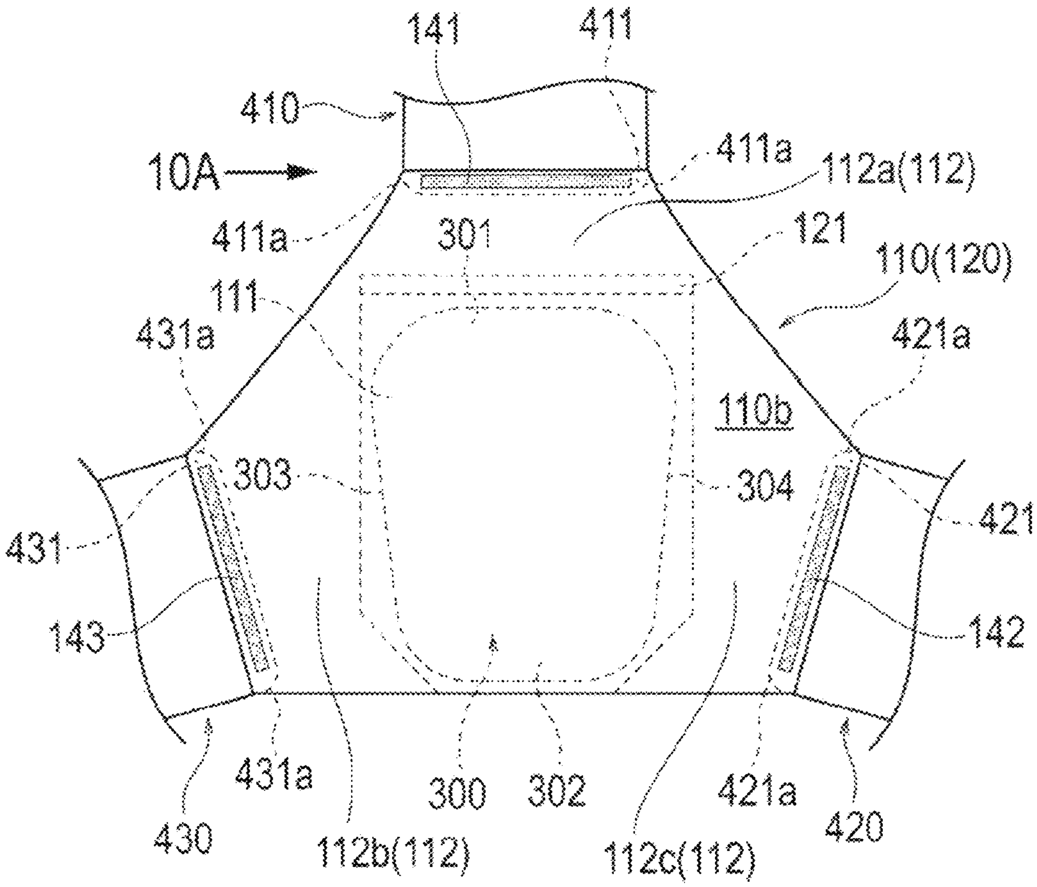
FIG. 9 is a view for describing a fused portion connecting each band body to the main body, and is a view briefly illustrating the outer surface side of the main body.
Figure 10:
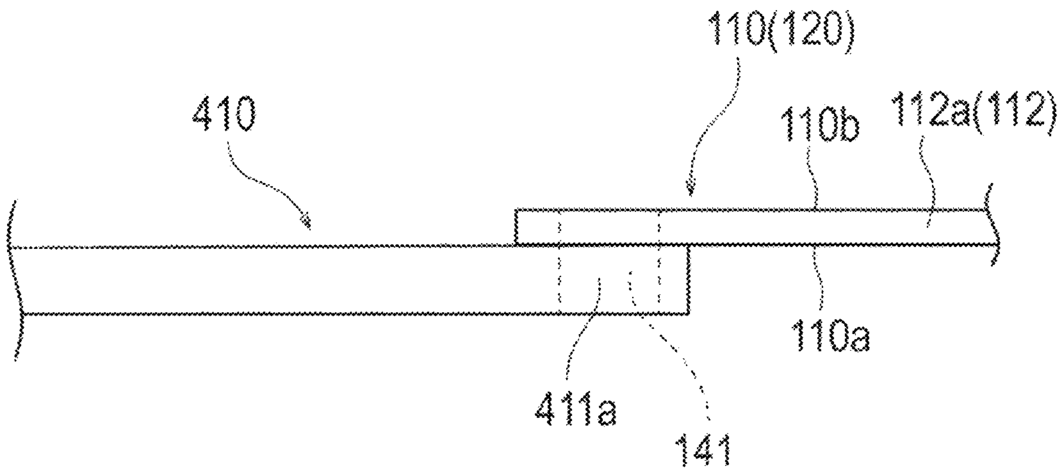
FIG. 10 is a view as seen in a direction of an arrow 10 illustrated in FIG. 9.

The main body 110 and the band bodies 410, 420, and 430 of the cover member 100 will be described in detail with reference to FIGS. 8, 9, and 10. FIG. 8 is a plan view of the inflatable member 210 as seen from the inner surface 110*a* side of the main body 110 (not illustrated). FIG. 9 is a plan view of the inflatable member 210 as seen from the outer surface 110*b* side of the main body 110 (not illustrated). FIG. 10 is a view as seen in a direction of an arrow 10A illustrated in FIG. 9.

Figure 1:
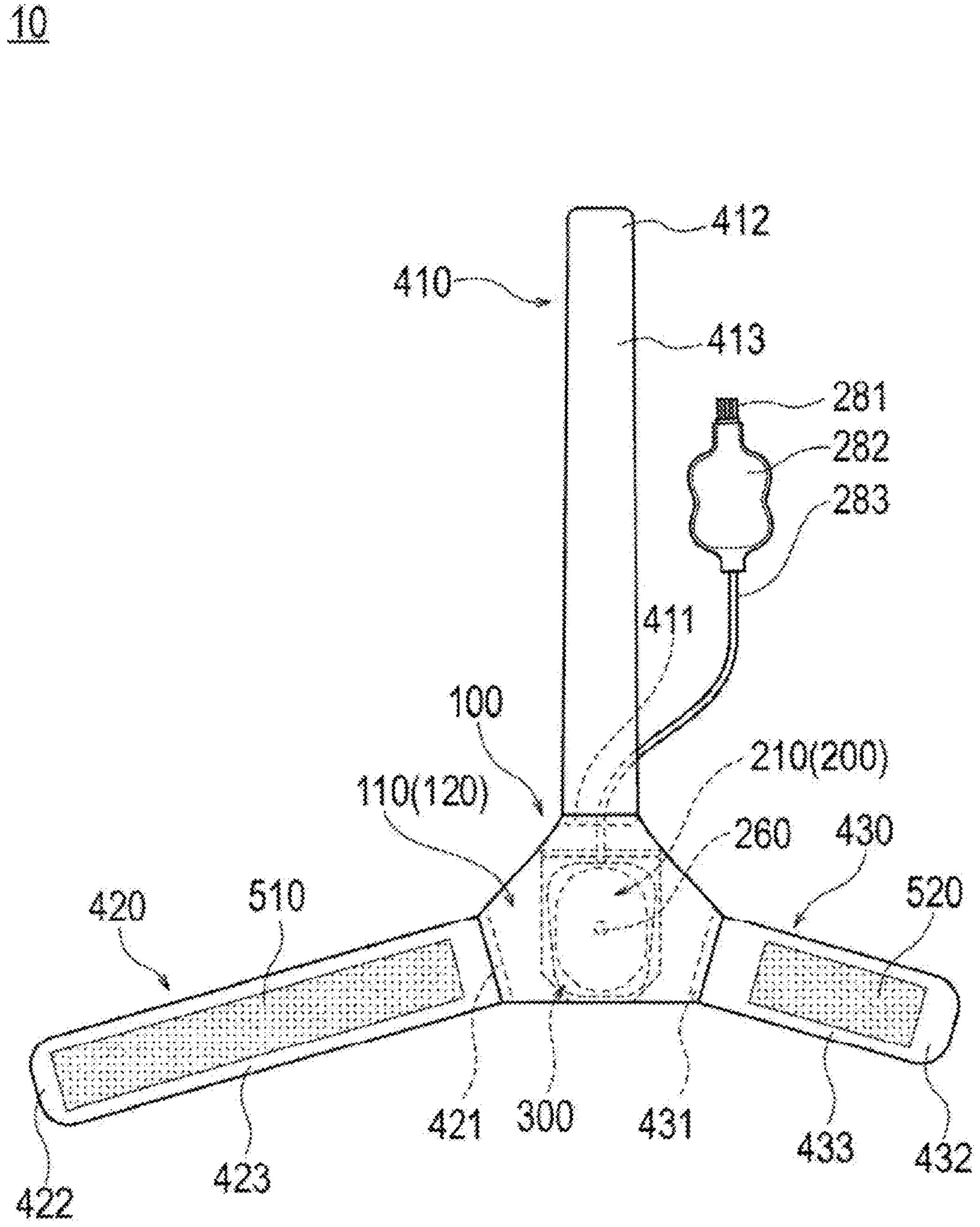
FIG. 1 is a view illustrating a hemostatic device according to an embodiment, and is a plan view seen from an outer surface side of each band body.

As illustrated in FIGS. 5, 8, and 9, the main body 110 includes a first region 111 where the support member 300 is located, and a second region 112 located between the first region 111 and each of the first band body 410, the second band body 420, and the third band body 430 in the plan view. FIG. 1 shows that the second and third band bodies 420, 430 are positioned such that a centerline of the second band body 420 and a centerline of the third band body 430 intersect one another in the first region 111 as seen in plan view, particularly the portion of the first region 111 overlying the support member 200.

As illustrated in FIGS. 5, 8, and 9, the second region 112 is located around the first region 111. Furthermore, the second region 112 is located between each two of the first band body 410, the second band body 420, and the third band body 430. Therefore, an edge portion of the main body 110 to which each of the first band body 410, the second band body 420, and the third band body 430 is connected is formed of the second region 112.

In the present embodiment, the second region 112 located between the first band body 410 and the first region 111 is referred to as a "second region 112*a*", the second region 112 located between the second band body 420 and the first region 111 is referred to as a "second region 112*b*", and the second region 112 located between the third band body 430 and the first region 111 is referred to as a "second region 112*c*".

The second region 112 can be made of a material having higher ductility than the support member 300. The material forming the second region 112 is not particularly limited as long as the material has higher ductility than the support member 300, but for example, the same material as that of the film-shaped member forming the inflatable member 210 described above can be used. For example, when the material of the film-shaped member forming the inflatable member 210 is polyvinyl chloride, polyvinyl chloride can be used for the second region 112 of the main body 110 similarly to the inflatable member 210. In such a case, as a constituent material from which the support member 300 may be fabricated, polycarbonate or the like, which is a material harder than polyvinyl chloride and has lower ductility than polyvinyl chloride, can be used.

As illustrated in FIG. 8, a width wm2 of the second region 112*b* and a width wm3 of the second region 112*c* decrease from the distal side (upper end 301 side) of the support member 300 to the proximal side (lower end 302 side) of the support member 300.

The width wm2 of the second region 112*b* is defined by a distance between the one end 421 of the second band body 420 and a virtual line VL1 along a side surface portion 303 located on the second band body 420 side of the support member 300 in the plan view illustrated in FIG. 8. Furthermore, the width wm3 of the second region 112*c* is defined by a distance between the one end 431 of the third band body 430 and a virtual line VL2 along a side surface portion 304 located on the third band body 430 side of the support member 300 in the plan view illustrated in FIG. 8.

As illustrated in FIG. 8, a width wm1 of the second region 112*a* is smaller than the width wm2 of the second region 112*b* and the width wm3 of the second region 112*c*. The width wm1 of the second region 112*a* is defined by a distance between the first end 121 and the one end 411 of the first band body 410 in the plan view illustrated in FIG. 8. The magnitude relationship between the width wm1 and each of the widths wm2 and wm3 can be defined by comparing the maximum width of the width wm1 with the maximum width of each of the widths wm2 and wm3 in the present specification.

As illustrated in FIG. 8, each of the side surface portions 303 and 304 of the support member 300 forms a first angle θ1 with respect to a center line A1 of the first band body 410. The center line A1 is an axis passing through a center of the first band body 410 in a width direction. FIG. 8 illustrates virtual lines A1' and A1" parallel to the center line A1 together with the center line A1 in order to clearly illustrate each of the angles θ1, θ2, and θ3.

When the first band body 410 does not have a substantially constant width along the extending direction, the center line A1 can be defined by a straight line connecting a center of the one end 411 of the first band body 410 in the width direction and a center of the other end 412 of the first band body 410 in the width direction. The above definition of the center line A1 similarly applies to a center line A2 of the second band body 420 and a center line A3 of the third band body 430.

The first angle θ1 is smaller than the angle θ2 formed by a straight line VL3 orthogonal to the center line A2 of the second band body 420 and the center line A1 (virtual line A1') of the first band body 410. The center line A2 is an axis passing through a center of the second band body 420 in the width direction.

The first angle θ1 is smaller than an angle θ3 formed by a straight line VL4 orthogonal to the center line A3 of the third band body 430 and the center line A1 (virtual line A1") of the first band body 410. The center line A3 is an axis passing through a center of the third band body 430 in the width direction.

As illustrated in FIGS. 9 and 10, each of the band bodies 410, 420, and 430 can be connected to the inner surface 110*a* of the main body 110.

Each of the band bodies 410, 420, and 430 can be secured to any position in a region surrounding the periphery of the retaining portion 130 in the main body 110.

Furthermore, each of the band bodies 410, 420, and 430 can be connected to a surface side (the inner surface 110*a* side) disposed on the body surface side of the right hand H1 in the above region. The one end 411 of the first band body 410 is secured on the inner surface 110*a* side of the main body 110 via a fused portion 141. In the present embodiment, as illustrated in FIG. 10, the fused portion 141 can be formed by applying heat from the outer surface 110*b* side of the main body 110 or the inner surface side of the first band body 410 in a state where the one end 411 is disposed to overlap the inner surface 110*a* side of the main body 110. Similarly, the one end 421 of the second band body 420 is secured to the inner surface 110*a* side of the main body 110 via a fused portion 142, and the one end 431 of the third band body 430 is secured to the inner surface 110*a* side of the main body 110 via a fused portion 143.

Parts where the fused portions 141, 142, and 143 are formed in the band bodies 410, 420, and 430, respectively, are harder than parts where the fused portions 141, 142, and 143 are not formed in the band bodies 410, 420, and 430, respectively. The fused portions 141, 142, and 143 are not illustrated in the drawings other than FIGS. 9 and 10.

As illustrated in FIGS. 9 and 10, in the first band body 410, ends 411*a* of side surfaces located on both sides in the width direction of the first band body 410 are not secured to the main body 110. That is, the fused portion 141 is formed only in a certain range excluding both sides of the one end 411 in the width direction. Similarly, ends 421*a*, of side surfaces located on both sides in the width direction of the second band body 420, in the second band body 420 are not secured to the main body 110, and ends 431*a*, of side surfaces located on both sides in the width direction of the third band body 430, in the third band body 430 are not secured to the main body 110. The one ends 411, 421, and 431 can be configured such that the fused portions 141, 142, and 143, respectively, are not formed in a range within 1 mm on both sides in the width direction, for example. That is, the one end 411, 421 and 431 of each of the band bodies 410, 420, 430 may be configured such that there is an unfused portion up to 1 mm on both sides, in the width-wise direction, of each end 141, 142, 143.

For example, as illustrated in FIG. 22, when the patient moves to twist the wrist the dorsal side of the right hand H1 or the like in the state where the hemostatic device 10 is worn on the right hand H1 of the patient, the ends 411*a*, 421*a*, and 431*a* located on the side surfaces of the band bodies 410, 420, and 430, respectively, in the width direction are likely to come into contact with the body surface such as the right hand H1 and/or the wrist. If a fused portion is formed at each of the ends 411*a*, 421*a*, and 431*a*, when the patient moves to twist the wrist toward the dorsal side of the right hand H1 or the like, the fused portion comes into contact with the body surface, and thus, the patient may feel pain or discomfort. In the hemostatic device 10, since the fused portions 141, 142, and 143 are not formed at the ends 411*a*, 421*a*, and 431*a* located on the side surfaces of the band bodies 410, 420, and 430, respectively, in the width direction, it is possible to prevent the occurrence of the above-described problem in advance.

A specific method of connecting (securing) each of the band bodies 410, 420, and 430 to the main body 110 is not particularly limited. Furthermore, even in a case where fusion bonding is selected as a method of connecting (securing) each of the band bodies 410, 420, and 430 to the main body 110, a range of the fusion bonding and the like can be arbitrarily changed.

As described above, a fusion bonding method of a "lap joint" in which fusion bonding is performed by applying heat from the outer surface 110*b* side of the main body 110 or the inner surface side of each of the band bodies 410, 420, and 430 in a state where each of the one ends 411, 421, and 431 overlaps the inner surface 110*a* of the main body 110 is adopted in the hemostatic device 10. However, a specific method of fusion-bonding each of the one ends 411, 421, and 431 to the inner surface 110*a* of the main body 110 is not particularly limited. As a method of fusion-bonding each of the one ends 411, 421, and 431 to the inner surface 110*a* of the main body 110, a known method of fusion-bonding two or more members can be appropriately adopted. As such a method, for example, a fusion bonding method such as a "stepped-lap joint" or a "butt joint" can be adopted in addition to the "lap joint".

The first band body 410, the second band body 420, and the third band body 430 can be made of a material that has high flexibility than the support member 300 and has lower ductility than a material of the second region 112.

For example, in a case where the support member 300 is made of any of materials to be described later and the second region 112 is made of any of the above-described materials, each of the band bodies 410, 420, and 430 can be made of a vinyl chloride resin, a polyurethane resin, a polyester resin, a polyamide resin, or the like. For example, in a case where the constituent material from which the support member 300 is fabricated is polycarbonate, each of the band bodies 410, 420, and 430 is made of a polyester resin or a polyamide resin having higher flexibility than polycarbonate. Furthermore, in a case where the material of each of the band bodies 410, 420, and 430 is made of a polyester resin or a polyamide resin, the second region 112 of the main body 110 can be made of polyvinyl chloride or the like as a material having higher ductility than the polyester resin or the polyamide resin. Furthermore, a shape, a length, a thickness, and the like of each of the band bodies 410, 420, and 430 are not particularly limited.

Each of the band bodies 410, 420, and 430 can be made of a material having higher flexibility than the support member 300 as described above. Furthermore, each of the band bodies 410, 420, and 430 is secured to the main body 110 on the inner surface 110*a* side of the main body 110. Therefore, the hemostatic device 10 is disposed such that the one ends 411, 421, and 431 of the band bodies 410, 420, and 430 come into contact with the body surface of the right hand H1 in the state where the hemostatic device 10 is worn on the right hand H1 of the patient, and the main body 110 is disposed to overlap thereon. Therefore, since the hemostatic device 10 is disposed such that each of the band bodies 410, 420, and 430 configured to be more flexible comes into contact with the body surface, it is possible to suppress the patient from feeling pain or the like when the vicinity of a region where the main body 110 is connected to each of the band bodies 410, 420, and 430 comes into contact with the body surface of the patient. It is more preferable that each of the band bodies 410, 420, and 430 is made of a material having higher flexibility than the main body 110 in order to improve the above effect in the hemostatic device 10. For example, when the material of the second region 112 of the main body 110 is made of polyvinyl chloride, a polyester resin or a polyamide resin having higher flexibility than polyvinyl chloride can be used as the material of each of the band bodies 410, 420, and 430. At this time, as the polyvinyl chloride forming the second region 112 of the main body 110, a resin having higher ductility than the polyester resin or the polyamide resin forming each of the band bodies 410, 420, and 430 is preferably used.

Furthermore, the second region 112 of the main body 110 can be made of a material having higher ductility than each of the band bodies 410, 420, and 430. Therefore, the hemostatic device 10 can provide the second region 112 with appropriate mobility.

Four securing parts, that is, a first securing part 510, a second securing part 520, a third securing part 530, and a fourth securing part 540, which enable the cover member 100 to be secured on the right hand H1, are disposed in the band bodies 410, 420, and 430.

As illustrated in FIG. 1, the first securing part 510 is disposed on an outer surface of the main body 423 of the second band body 420.

As illustrated in FIG. 1, the second securing part 520 is disposed on an outer surface of the main body 433 of the third band body 430.

Figure 2:
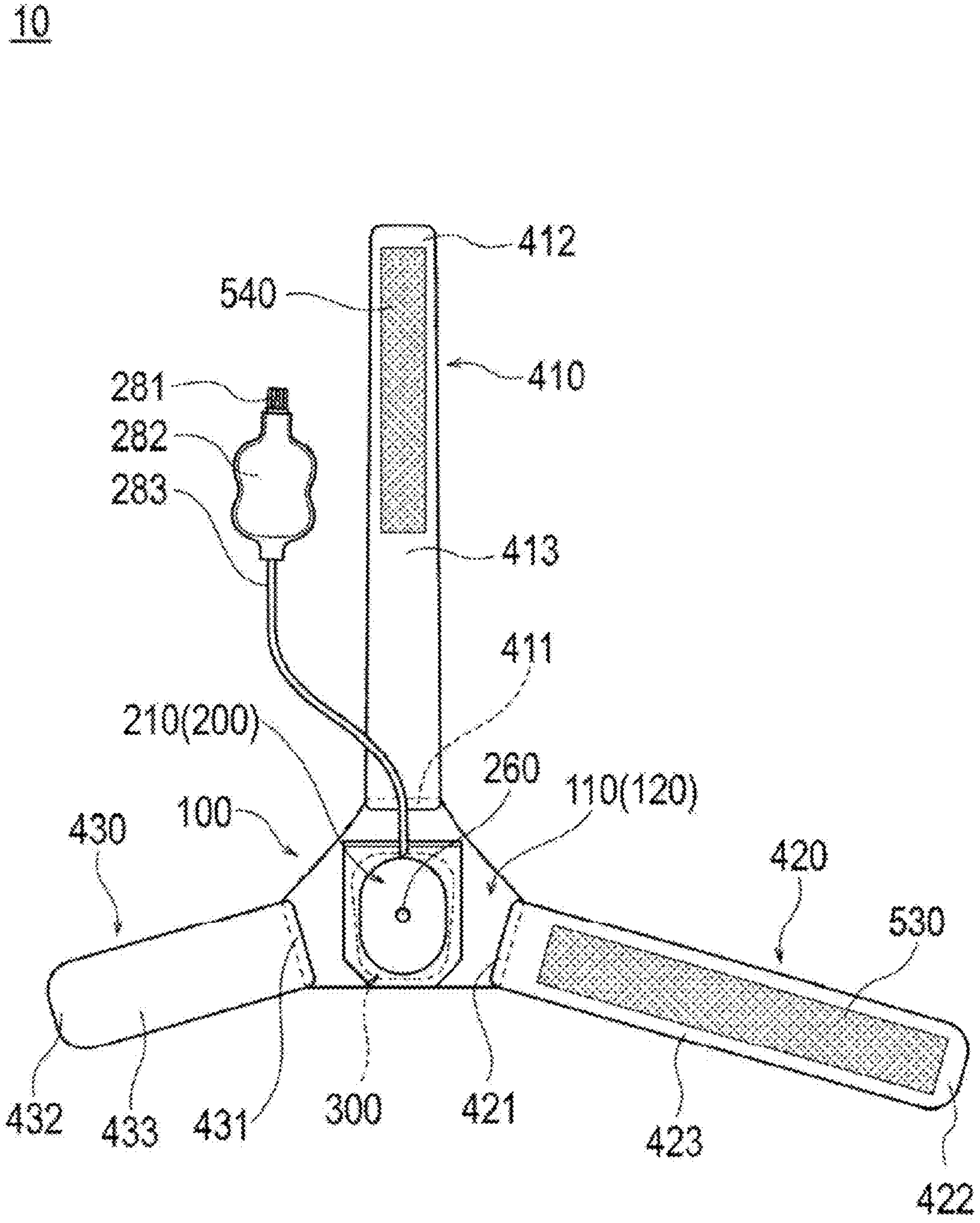
FIG. 2 is a view illustrating the hemostatic device according to the embodiment, and is a plan view seen from an inner surface side of each band body.
Figure 3:
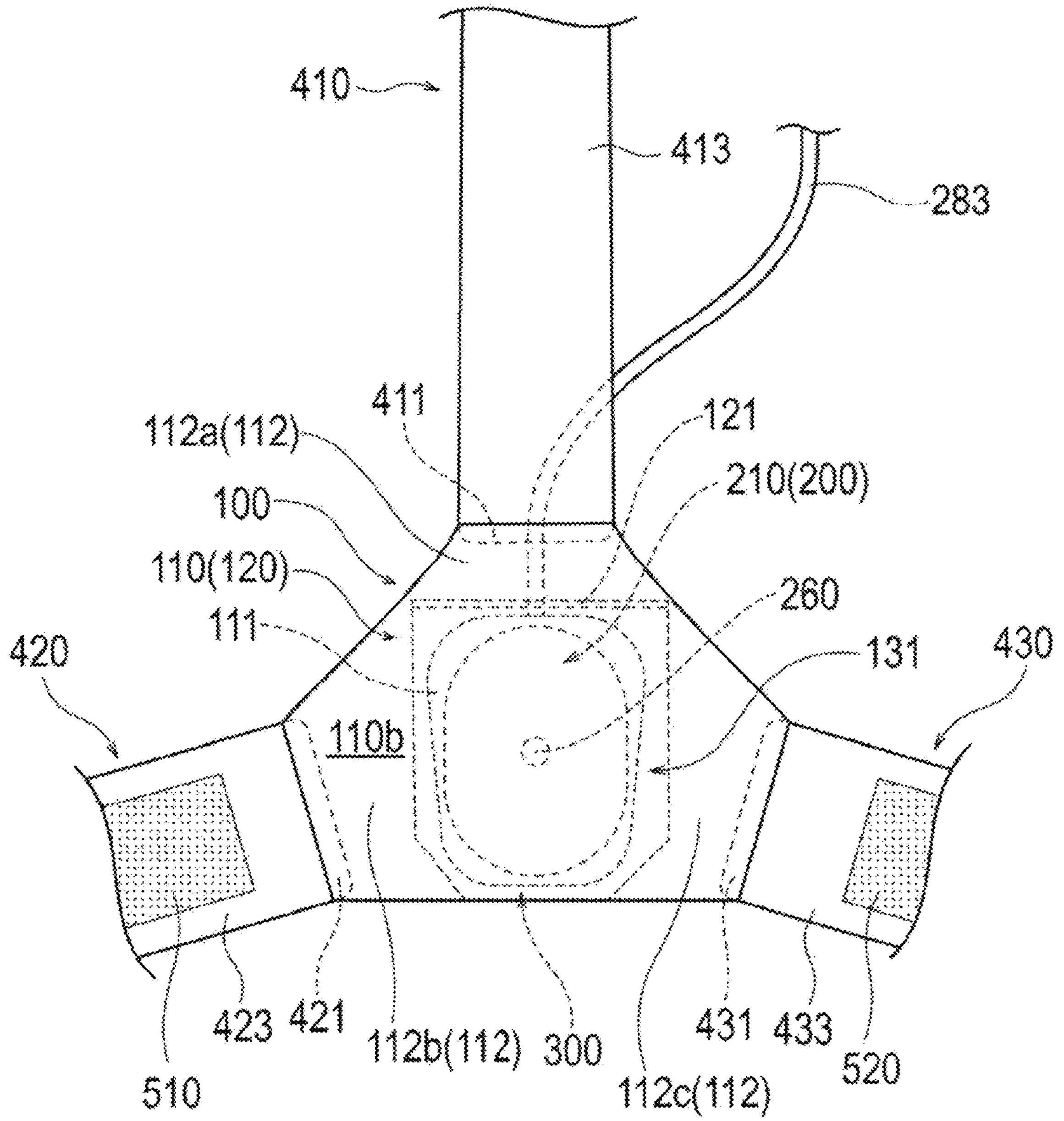
FIG. 3 is an enlarged view illustrating a part of the hemostatic device as seen from an outer surface side of a main body of a cover member.

As illustrated in FIG. 2, a third securing part 530 is disposed on an inner surface of the main body 423 of the second band body 420.

As illustrated in FIG. 2, a fourth securing part 540 is disposed on an inner surface of the main body 413 of the first band body 410.

The inner surface of each of the band bodies 410, 420, and 430 is a surface disposed on the body surface of the right hand H1 in the state where the hemostatic device 10 is worn on the right hand H1 of the patient.

The outer surface of each of the band bodies 410, 420, and 430 is a surface located opposite to the inner surface.

The first securing part 510 and the second securing part 520 are formed of a male side of a hook-and-loop fastener. The third securing part 530 and the fourth securing part 540 are formed of a female side of the hook-and-loop fastener. The hook-and-loop fastener in the present specification is a hook-and-loop fastener, and is, for example, Magic Tape (registered trademark) or Velcro (registered trademark).

The second band body 420 and the third band body 430 are configured to be detachably attached via the third securing part 530 located on the inner surface of the main body 423 of the second band body 420 and the second securing part 520 located on the outer surface of the main body 433 of the third band body 430. Furthermore, the first band body 410 and the second band body 420 are configured to be detachably attached via the fourth securing part 540 located on the inner surface of the main body 413 of the first band body 410 and the first securing part 510 located on the outer surface of the main body 423 of the second band body 420.

A specific structure of each of the securing parts 510, 520, 530, and 540 is not limited as long as the cover member 100 can be secured on the right hand H1 by connecting the band bodies 410, 420, and 430 to each other in a state where the hemostatic device 10 is disposed on the right hand H1. For example, omission of installation of some securing parts, a change of a position where the securing part is disposed in each of the band bodies 410, 420, and 430, and the like can be arbitrarily performed. Furthermore, in a case where each of the securing parts 510, 520, 530, and 540 is formed of the hook-and-loop fastener, the male side and the female side of the hook-and-loop fastener may be interchanged. Furthermore, the securing parts 510, 520, 530, and 540 may be configured using, for example, coupling mechanisms or the like including a frame portion in which a snap, a button, a clip, or a protrusion is formed and an engaged portion in which a hole engageable with the frame portion is formed.

<Support Member>

FIGS. 11 to 15 illustrate the support member 300. In the drawing, arrows X1 and X2 indicate a longitudinal direction of the support member 300 (the same direction as the direction of the longitudinal width wa of the inflatable member 210), arrows Y1 and Y2 indicate a width direction of the support member 300 (the same direction as the direction of the lateral width wb of the inflatable member 210), and arrows Z1 and Z2 indicate a thickness direction of the support member 300.

As illustrated in FIG. 6, the support member 300 can be disposed in the insertion portion g of the retaining portion 130.

As illustrated in FIGS. 4, 5, 11, 12, and 13, the support member 300 includes the upper end 301 that is located on the first band body 410 side and forms an end of the support member 300, the lower end 302 forming an end opposite to the upper end 301, and the pair of side surface portions 303 and 304 connecting the upper end 301 and the lower end 302.

As illustrated in FIGS. 19 and 22, the upper end 301 can be disposed on the fingertip side (distal side) of the finger in the state where the hemostatic device 10 is worn on the right hand H1 of the patient. The lower end 302 can be disposed on the forearm Ar side (proximal side) in the state where the hemostatic device 10 is worn on the right hand H1 of the patient. The upper end 301 forms a distal portion of the support member 300, and the lower end 302 forms a proximal portion of the support member 300.

The upper end 301 of the support member 300 has a linear flat portion 301*a* in the plan view illustrated in FIG. 11. The flat portion 301*a* extends substantially linearly between corners 306*c* and 306*d* located on the upper end 301 side.

The lower end 302 of the support member 300 has a linear flat portion 302*a* in the plan view illustrated in FIG. 11.

The flat portion 302*a* extends substantially linearly between corners 306*a* and 306*b* located on the lower end 302 side.

The support member 300 has an intermediate portion 305 located between the upper end 301 and the lower end 302 in the plan view illustrated in FIG. 11. The intermediate portion 305 is located in the middle in the longitudinal direction connecting the upper end 301 and the lower end 302.

Figure 12:
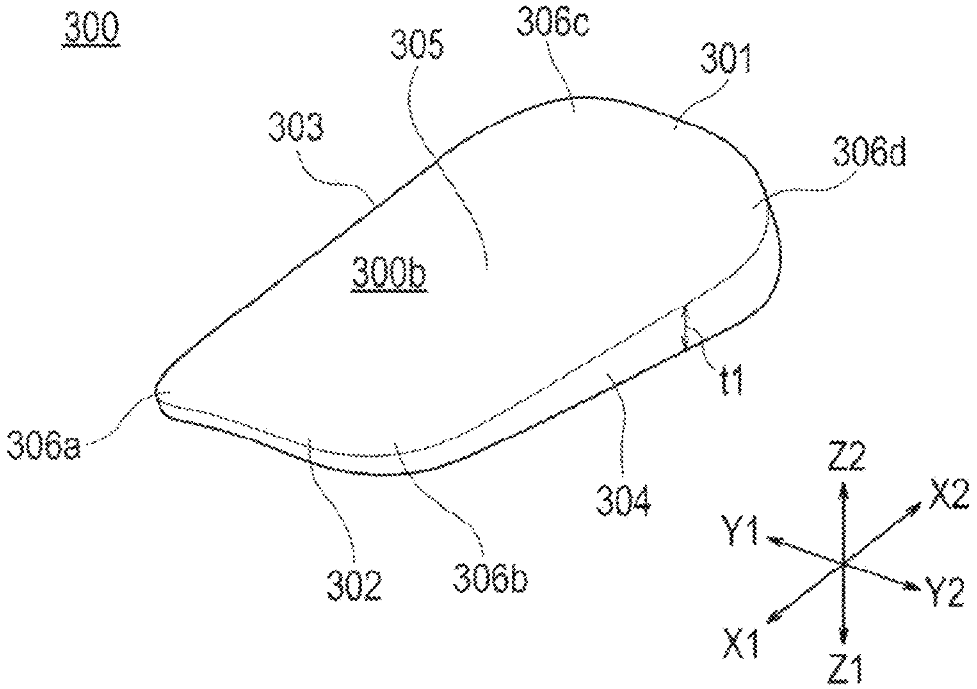
FIG. 12 is a perspective view of the support member as seen from a lower end side.
Figure 13:
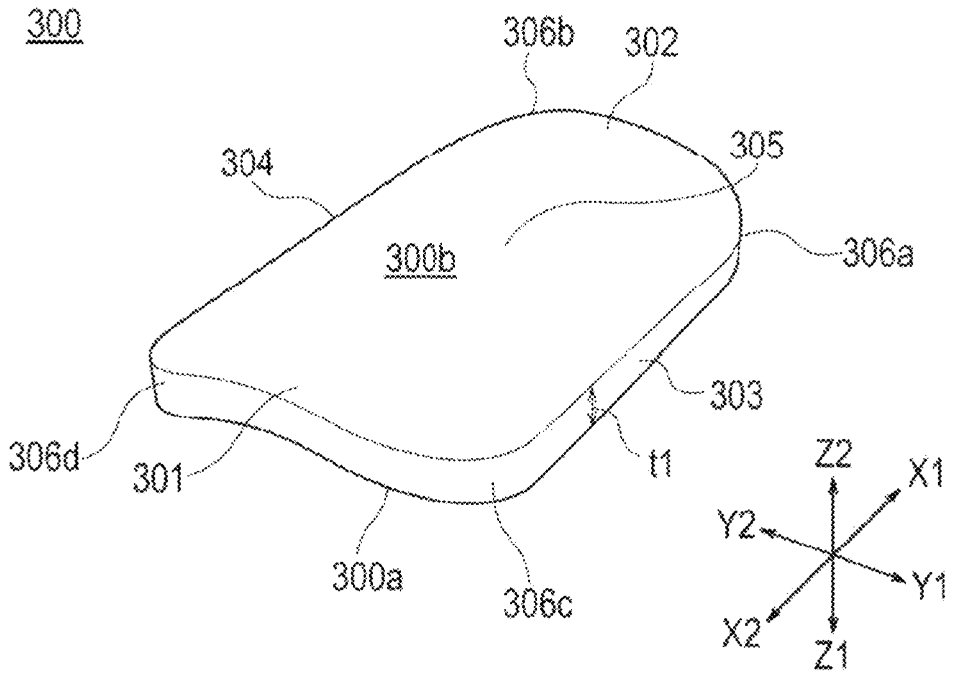
FIG. 13 is a perspective view of the support member as seen from an upper end side.

As illustrated in FIGS. 7, 12, and 13, the outer surface 300*b* of the support member 300 is curved toward the second band body 420 and the third band body 430.

The outer surface 300*b* of the support member 300 can be formed to have a substantially constant radius of curvature at each portion in the longitudinal direction of the support member 300, for example.

As illustrated in FIG. 11, the support member 300 has a line-symmetrical shape with respect to the center line A1 of the first band body 410 in the main body 110. In the present embodiment, the support member 300 has a bilaterally symmetrical shape with respect to a line segment that is orthogonal to an axis along a width w1 of the upper end 301 and passes through a point where distances from both ends in a direction of the width w1 of the upper end 301 are equal in the plan view of FIG. 11. Therefore, the support member 300 can be disposed on the main body 110 so as to be bilaterally symmetrical with respect to the center line A1 of the first band body 410.

Each of the side surface portions 303 and 304 has a line-symmetrical shape with respect to the center line A1 of the first band body 410 in the main body 110. Each of the side surface portions 303 and 304 extends to be bilaterally symmetrical with respect to the center line A1 such that the width of the support member 300 decreases at a substantially constant rate from the upper end 301 side to the lower end 302 side in the plan view of FIG. 8.

The support member 300 is located to have the center of gravity G1 of the outer shape of the support member 300 in the plan view illustrated in FIG. 8.

The width w1 of the upper end 301 is formed to be larger than a width w2 of the lower end 302 such that the center of gravity G1 is located on the upper end 301 side of the intermediate portion 305. In the present embodiment, the support member 300 has a substantially trapezoidal shape in which the width w1 of the upper end 301 is larger than the width w2 of the lower end 302. Therefore, the center of gravity G1 of the support member 300 is located at a position shifted from the intermediate portion 305 of the support member 300 to the upper end 301 side (a lower bottom side of the trapezoidal shape) by a predetermined distance.

In the present embodiment, the width w1 of the upper end 301 of the support member 300 is defined by a dimension (maximum width) of a part having the largest width in a region located on the upper end 301 side of the intermediate portion 305 of the support member 300. Furthermore, the width w2 of the lower end 302 of the support member 300 can be defined by a length of a straight line connecting a boundary between the side surface portion 303 and the corner 306*a* and a boundary between the side surface portion 304 and the corner 306*b*. In a case where the corner 306*a* is formed in a curved shape as in the present embodiment, the boundary between the side surface portion 303 and the corner 306*a* is a position where a tangent line of the side surface portion 303 starts to change in a curved manner. Similarly, in a case where the corner 306*b* is formed in a curved shape as in the present embodiment, the boundary between the side surface portion 304 and the corner 306*b* is a position where a tangent line of the side surface portion 304 starts to change in a curved manner. In a case where the corners 306*a* and 306*b* are not formed in the curved shape, the width w2 of the lower end 302 of the support member 300 can be defined by a length of a straight line connecting apexes located at the corners 306*a* and 306*b*.

In the hemostatic device 10, the width of the support member 300 decreases from the upper end 301 toward the lower end 302. Therefore, the hemostatic device 10 can secure the widths wm2 and wm3 of the second regions 112*b* and 112*c* located near the lower end 302 of the support member 300 to a predetermined size. In the hemostatic device, the widths wm2 and wm3 of the respective second regions near the lower end become excessively small, for example, in a case where the support member is formed in a square or rectangular shape having a substantially constant width from the upper end to the lower end or formed in a trapezoidal shape having a width increasing from the upper end to the lower end.

In such a case, the mobility in the second regions located near the ends 421 and 431 of the band bodies 420 and 430 is greatly reduced. In particular, in the hemostatic device 10, each of the band bodies 420 and 430 is configured to extend to be inclined toward the proximal side of the cover member 100 with the center c1 of the inflatable member 210 as a reference in order to easily wrap each of the band bodies 420 and 430 around the right hand H1 of the patient. Therefore, when the support member is formed in the square shape or the rectangular shape, or in the trapezoidal shape having the width increasing from the upper end to the lower end as described above, the widths wm2 and wm3 of the respective second regions near the lower end of the support member are necessarily formed to be extremely small. As a result, it is difficult to sufficiently secure the mobility of each second region in the hemostatic device. That is, the moveability or flexibility of the second regions 112*a*, 112*b*, 112*c* in the hemostatic device (i.e., the ability of the second regions to move or flex) may be diminished. As described above, the hemostatic device 10 is preferably configured to secure the widths wm2 and wm3 of the second regions 112*b* and 112*c* near the lower end 302 to such an extent that the band bodies 410, 420, and 430 do not interfere with the support member 300 when the second regions 112*b* and 112*c* are deformed near the lower end 302. For example, the width wm2 of the second region 112*b* can be configured to be about half from an end located on the distal side of the second band body 420 to an end located on the proximal side of the second band body 420. Similarly, the width wm3 of the second region 112*c* can be configured to be about half from an end located on the distal side of the third band body 430 to an end located on the proximal side of the third band body 430.

Furthermore, the first angle θ1 formed by each of the side surface portions 303 and 304 of the support member 300 and the center line A1 of the first band body 410 is smaller than the second angle θ2 formed by the straight line VL3 orthogonal to the center line A2 of the second band body 420 and the center line A1 of the first band body 410, and is smaller than the third angle θ3 formed by the straight line VL4 orthogonal to the center line A3 of the third band body 430 and the center line A1 of the first band body 410 (see FIG. 8). Therefore, the hemostatic device 10 is configured such that each of the widths wm2 and wm3 gradually decreases from the distal side to the proximal side (from the upper end 301 side to the lower end 302 side) of the support member 300 according to a difference in angle between the first angle θ1 and each corresponding one of the angles θ2 and θ3. Therefore, when the second band body 420 and the third band body 430 of the hemostatic device 10 are wrapped around the right hand H1 of the patient, the second regions 112*b* and 112*c* located on the proximal side of the support member 300 can be prevented from being excessively moved. Therefore, when the second band body 420 and the third band body 430 of the hemostatic device 10 are wrapped around the right hand H1 of the patient, positions where the second band body 420 and the third band body 430 are wrapped around the right hand H1 of the patient can be prevented from being shifted to the proximal side of the support member 300. In a case where the first angle θ1 is substantially the same as the second angle θ2 in the hemostatic device, the widths wm2 and wm3 are formed to be substantially constant from the distal side to the proximal side of the support member, and thus, it is difficult to effectively prevent the positions where the second band body and the third band body are wrapped around the right hand H1 of the patient from being shifted to the proximal side of the support member. Furthermore, in a case where the first angle θ1 is larger than the second angle θ2, the hemostatic device 10 is formed such that the widths wm2 and wm3 increase from the distal side to the proximal side of the support member 300, and thus, it is difficult to effectively prevent the positions where the second band body and the third band body are wrapped around the right hand H1 of the patient from being shifted to the proximal side of the support member.

Figure 14:
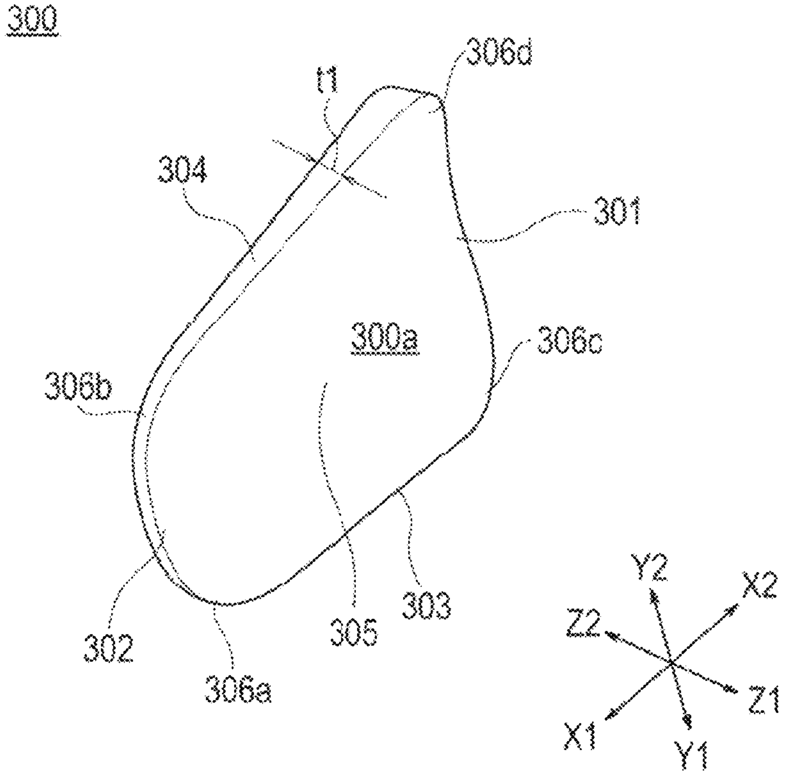
FIG. 14 is a perspective view illustrating an inner surface side of the support member.
Figure 15:
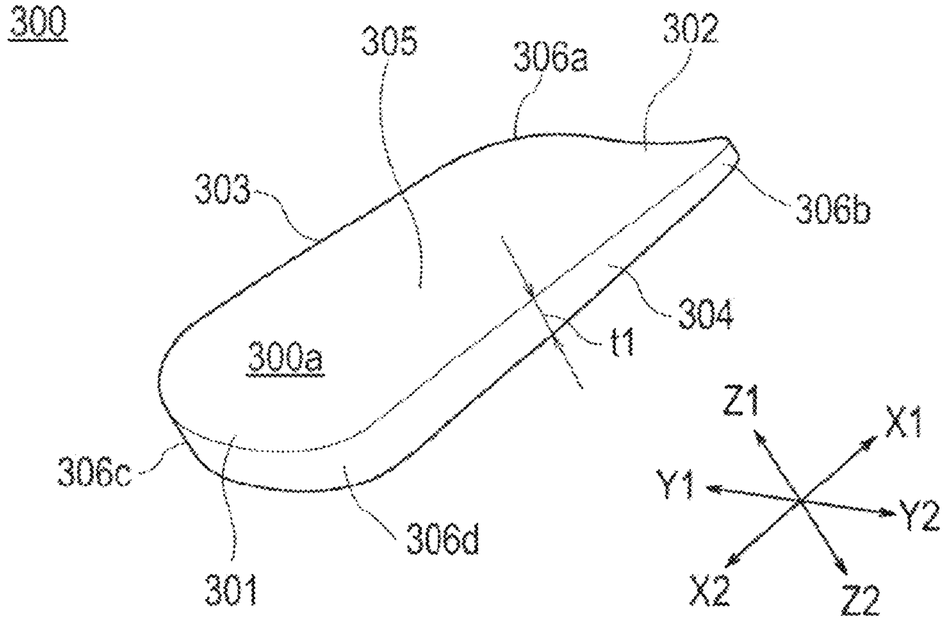
FIG. 15 is a perspective view illustrating the inner surface side of the support member.

The inner surface 300*a* of the support member 300 is curved toward the second band body 420 and the third band body 430. That is, as illustrated in FIGS. 7, 14, and 15, the inner surface 300*a* of the support member 300 is curved in a shape projecting in a direction away from the inflatable member 210.

The inner surface 300*a* of the upper end 301 of the support member 300 can be formed to have a radius of curvature smaller than a radius of curvature of the inner surface 300*a* of the lower end 302 of the support member 300, for example.

As illustrated in FIGS. 12, 13, 14, and 15, the support member 300 is configured such that a thickness t1 of each of the side surface portions 303 and 304 connecting the upper end 301 and the lower end 302 becomes thinner from the upper end 301 to the lower end 302. Therefore, the support member 300 is inclined such that a distance between the outer surface 300*b* and the inner surface 300*a* decreases from the upper end 301 to the lower end 302 in the cross-sectional view illustrated in FIG. 6 and a cross-sectional view illustrated in FIG. 20.

Each of the corners 306*a*, 306*b*, 306*c*, and 306*d* located at the four corners of the support member 300 is formed in a curved shape that is rounded.

The hemostatic device 10 is preferably formed such that a part where the marker portion 260 of the inflatable member 210 is provided, a part overlapping the marker portion 260 in the cover member 100 (the upper surface region 131 and the lower surface region 132 of the retaining portion 130), and a part overlapping the marker portion 260 in the support member 300 are transparent. In a case where each of the members 100, 210, and 300 is configured in this manner, an operator can easily visually confirm a position of the marker portion 260 disposed on the inflatable member 210 and/or the first puncture site p1 via the parts formed to be transparent in the members 100, 210, and 300 when the hemostatic device 10 is worn on the right hand H1 of the patient as illustrated in FIGS. 17 to 19. The term "transparent" in the present specification includes colored transparent, colorless transparent, and translucent.

In the hemostatic device 10, the entire main body 110 including the first region 111 and the second region 112 surrounding the periphery of the first region 111 is preferably made of a transparent material. In the main body 110, the second region 112 can be configured as a window portion that transmits light to the inner surface 110*a* side of the main body 110 by forming the second region 112 using the transparent material. Since the second region 112 is configured as the window portion in the hemostatic device 10, a sufficient amount of light can enter the inner surface 110*a* side of the main body 110 when the hemostatic device 10 is worn on the right hand H1 of the patient. Therefore, when the hemostatic device 10 is worn on the right hand H1 of the patient, the operator can suitably perform alignment of the marker portion 260 and the first puncture site p1 or the like with the light entering through the second region 112 (window portion). In addition, the operator can visually confirm the position of the marker portion 260 and/or the first puncture site p1 easily in the state where the hemostatic device 10 is worn on the right hand H1 of the patient. Furthermore, the main body 110 is more preferably made of transparent polyvinyl chloride. The main body 110 made of polyvinyl chloride is excellent in processability. With such a configuration, the amount of light to enter the inner surface 110*a* side of the main body 110 can be easily adjusted by applying coloring or design with respect to the main body 110. Therefore, the hemostatic device 10 can achieve both visibility of the marker portion 260 and/or the first puncture site p1 and design quality.

As the constituent material from which the support member 300 may be fabricated when the inflatable member 210 is made of the above-described material, for example, acrylic resin, polyvinyl chloride (particularly hard polyvinyl chloride), polyolefin such as polyethylene, polypropylene, or polybutadiene, polystyrene, poly-(4-methylpentene-1), polycarbonate, ABS resin, polymethyl methacrylate (PMMA), polyacetal, polyacrylate, polyacrylonitrile, polyvinylidene fluoride, ionomer, acrylonitrile-butadiene-styrene copolymer, polyethylene terephthalate (PET), or the like, can be used. For example, when the material of the film-shaped member forming the inflatable member 210 is polyvinyl chloride, polycarbonate or the like, which is a material harder than the polyvinyl chloride, can be used as the constituent material from which the support member 300 may be fabricated.

<Injection Portion>

As illustrated in FIGS. 1 and 2, the hemostatic device 10 has an injection portion 281 for injecting a fluid into the inflatable member 210.

The injection portion 281 is formed of a connector incorporating a check valve (not illustrated). A syringe (not illustrated) may be connected to the injection portion 281.

A buffer member 282 having an inflatable space is disposed between the injection portion 281 and the inflatable member 210. The buffer member 282 is formed of a flexible bag-shaped member in which a space is formed.

The buffer member 282 may be provided with an arrow-shaped marker indicating an insertion direction of the syringe into the injection portion 281.

The injection portion 281 is connected to one end side of the buffer member 282. A lumen of the injection portion 281 communicates with the space of the buffer member 282. However, while the check valve incorporated in the injection portion 281 is closed, communication between the lumen of the injection portion 281 and the space of the buffer member 282 is blocked.

The tube 283 having flexibility is connected to the other end side of the buffer member 282. A lumen of the tube 283 communicates with the space of the buffer member 282. Furthermore, the other end of the tube 283, opposite to the one end connected to the buffer member 282, is connected to the inflatable member 210. The lumen of the tube 283 communicates with the inner cavity 210*a* of the inflatable member 210.

To inflate the inflatable member 210, the operator inserts a cylindrical distal end portion of the syringe (not illustrated) into the injection portion 281 and opens the check valve. The operator injects air in the syringe into the inner cavity 210*a* of the inflatable member 210 by pushing a pusher of the syringe in a state where the check valve of the injection portion 281 is opened.

When the air is injected into the inner cavity 210*a* of the inflatable member 210, the inflatable member 210 inflates. When the inflatable member 210 inflates, the buffer member 282 communicating with the inner cavity 210*a* of the inflatable member 210 via the tube 283 expands. The operator can easily grasp or understand that the inflatable member 210 inflates without leakage of air by visually confirming the expansion of the buffer member 282.

To deflate the inflatable member 210, the operator inserts the cylindrical distal end portion of the syringe into the injection portion 281 and pulls the pusher of the syringe. The operator can discharge the air in the inner cavity 210*a* of the inflatable member 210 to the syringe by performing the above operation.

The injection portion 281, the buffer member 282, and the tube 283 may be prepared and provided in a state of being coupled to the inflatable member 210, or may be prepared and provided in a state of being separated from the inflatable member 210. Furthermore, a specific configuration or the like of the injection portion 281 is not particularly limited as long as the supply of the fluid to the inner cavity 210*a* of the inflatable member 210 and the discharge of the fluid from the inner cavity 210*a* of the inflatable member 210 can be controlled.

<Use Example of Hemostatic Device>

Next, a use example of the hemostatic device 10 will be described with reference to FIGS. 16 to 22.

Hereinafter, a process of using the hemostatic device 10 to stop bleeding at the first puncture site p1 formed on the right hand H1 of the patient illustrated in FIG. 16 will be described.

FIG. 17 illustrates a state where various procedures performed using the sheath tube 610 of the introducer 600 inserted into the first puncture site p1 are completed.

When causing the hemostatic device 10 to be worn on the right hand H1 of the patient, the operator disposes the inflatable member 210 and the support member 300 so as to overlap the first puncture site p1 as illustrated in FIG. 17. At this time, the operator can appropriately align the inflatable member 210 and the support member 300 with the first puncture site p1 by disposing the marker portion 260 at the first puncture site p1 while visually confirming a position of the marker portion 260 disposed at the inflatable member 210.

When causing the hemostatic device 10 to be worn on the right hand H1 of the patient, the operator can dispose the support member 300 so as to overlap the metacarpal bone B1 of the index finger and the metacarpal bone B2 of the thumb. An interval between the metacarpal bone B1 of the index finger and the metacarpal bone B2 of the thumb gradually narrows from the fingertip side to the forearm Ar side (see FIG. 16).

A width of the support member 300 decreases from the upper end 301 disposed on the fingertip side to the lower end 302 disposed on the forearm Ar side (see FIG. 11). Therefore, the operator can dispose the support member 300 along the metacarpal bones B1 of the index finger and the metacarpal bones B2 of the thumb by disposing the support member 300 so as to overlap the metacarpal bones B1 of the index finger and the metacarpal bones B2 of the thumb from the dorsal side of the right hand H1 of the patient. The operator can prevent a gap from being formed between the inflatable member 210 disposed on the inner surface 300*a* side of the support member 300 and the right hand H1 by disposing the support member 300 along the metacarpal bone B1 of the index finger and the metacarpal bone B2 of the thumb.

As illustrated in FIG. 18, the operator wraps the second band body 420 and the third band body 430 along the outer periphery of the right hand H1 of the patient. The operator can connect the second band body 420 and the third band body 430 via the securing parts 520 and 530 by bringing the third securing part 530 (see FIG. 2) disposed on the inner surface of the second band body 420 into contact with the second securing part 520 (see FIG. 1) disposed on the outer surface of the third band body 430. The operator can firmly wrap each of the band bodies 420 and 430 along the outer periphery of the right hand H1 by connecting the band bodies 420 and 430 to each other in a state where the support member 300 overlaps the metacarpal bone B1 of the index finger and the metacarpal bone B2 of the thumb.

FIGS. 23 and 24 illustrate a state where the second region 112*c* is deformed at the time of wrapping the third band body 430 around the right hand H1 of the patient. In the hemostatic device 10, the second region 112*c* is made of a material having higher ductility than the support member 300 located on the first region 111. Therefore, the second region 112*c* has high mobility that allows the third band body 430 to move with respect to the support member 300. When wrapping the third band body 430 around the right hand H1 of the patient, the operator can easily adjust wrapping positions of the band bodies 410 and 420 by moving the second region 112*c*. FIGS. 23 and 24 illustrate a state at the time of moving the second region 112*c*, and the second region 112*a* and the second region 112*b* similarly have high mobility that allows the band bodies 410 and 420 to move with respect to the support member 300.

The width wm2 of the second region 112*b* and the width wm3 of the second region 112*c* decrease from the distal side of the support member 300 to the proximal side of the support member 300 (see FIG. 8). Therefore, in each of the second regions 112*b* and 112*c*, a movable range in the width direction of each of the second regions 112*b* and 112*c* is smaller on the proximal side of the support member 300 than on the distal side of the support member 300. As a result, the hemostatic device 10 can prevent the second regions 112*b* and 112*c* located on the proximal side of the support member 300 from being excessively moved at the time of wrapping the band bodies 420 and 430 around the right hand H1. Therefore, it is possible to wrap the band bodies 420 and 430 along directions horizontal to each other while preventing the wrapping positions of the band bodies 420 and 430 from being greatly shifted to the proximal side of the support member 300 in the hemostatic device 10 at the time of wrapping the band bodies 420 and 430 around the right hand H1 of the patient. As a result, the hemostatic device 10 can enhance a force of securing the support member 300 and the inflatable member 210 with respect to the right hand H1 of the patient. Therefore, the hemostatic device 10 can improve a compressive force applied to the first puncture site p1 by the inflatable member 210 when the inflatable member 210 inflates.

The outer surface 300*b* of the support member 300 is curved toward the second band body 420 side (side surface portion 303 side) and the third band body 430 side (side surface portion 304 side) (see FIGS. 5, 7, 14, and 15). Therefore, the operator can press the support member 300 against the right hand H1 from the outer surface 300*b* side so as to be along the outer periphery of the right hand H1 as illustrated in FIG. 21 by wrapping the second band body 420 and the third band body 430 along the right hand H1 of the patient as illustrated in FIG. 18. Therefore, the hemostatic device 10 can enhance the force of securing the support member 300 and the inflatable member 210 with respect to the right hand H1 of the patient.

As illustrated in FIG. 19, the operator disposes a part of the first band body 410 on a palm side of the right hand H1 while passing the first band body 410 through the interdigital part fb located between the thumb and the index finger of the right hand H1 of the patient. At this time, the operator can connect the first band body 410 and the second band body 420 via the securing parts 510 and 540 by bringing the fourth securing part 540 (see FIG. 2) disposed on the inner surface of the first band body 410 into contact with the first securing part 510 (see FIG. 1) disposed on the outer surface of the second band body 420.

When disposing the first band body 410 in the interdigital part fb, the operator can flexibly deform the second region 112*a* (see FIG. 8) located between the first region 111 and the first band body 410. Therefore, the first band body 410 can be appropriately disposed through the interdigital part fb.

The first band body 410 extends in a direction substantially perpendicular to a direction in which the band bodies 420 and 430 extend in the main body 110. Therefore, there is a possibility that a sufficient tightening force cannot be applied to the first band body 410 at the time of wrapping the first band body 410 along the interdigital part fb. In the hemostatic device 10, the width wm1 of the second region 112*a* is smaller than the width wm2 of the second region 112*b* and the width wm3 of the second region 112*c* (see FIG. 8). Therefore, the second region 112*a* has a narrower movable range as compared with the other second regions 112*b* and 112*c*. Therefore, the hemostatic device 10 can suppress the second region 112*a* from being excessively extended when the first band body 410 is wrapped along the interdigital part fb. As a result, the hemostatic device 10 can secure the first band body 410 in a state of being firmly tightened to the interdigital part fb.

Furthermore, in the hemostatic device 10, the second region 112 is located around the first region 111, and the second region 112 is located between each two of the band bodies 410, 420, and 430. Therefore, the edge portion of the main body 110 connecting each of the band bodies 410, 420, and 430 is formed of the second region 112. Therefore, the hemostatic device 10 has a structure in which mobility is given between each two of the band bodies 410, 420, and 430 by the second region 112 located between each two of the band bodies 410, 420, and 430. Therefore, in the hemostatic device 10, the mobility of the second region 112 is further excellent. For example, in a case where the edge portion of the main body connecting each of the band bodies is covered with one end of the band body (in a case where the one end of the band body is connected by fusion bonding or adhesion along the edge portion of the main body 110 connecting each of the band bodies 410, 420, and 430), the mobility of the edge portion of the main body connecting each of the band bodies in the hemostatic device decreases. As a result, it is difficult to sufficiently enhance the mobility of the second region in the hemostatic device.

Furthermore, each of the second regions 112*a*, 112*b*, and 112*c* is located between each corresponding one of the band bodies 410, 420, and 430 and the first region 111 in the hemostatic device 10. Therefore, each of the band bodies 410, 420, and 430 can be disposed to be close to or in close contact with the body surface of the right hand H1 by flexibly deforming the second regions 112*a*, 112*b*, and 112*c* at the time of wrapping the band bodies 410, 420, and 430, respectively, around the right hand H1 of the patient. Therefore, the hemostatic device 10 can enhance the force of securing the inflatable member 210 and the support member 300 with respect to the right hand H1.

The support member 300 includes the upper end 301 and the side surface portions 303 and 304. The first band body 410 extends from the upper end 301 side, the second band body 420 extends from the side surface portion 303 side, and the third band body 430 extends from the side surface portion 304 side (see FIG. 5). Therefore, the hemostatic device 10 can secure the support member 300 to the right hand H1 of the patient in a state where a uniform force is applied to positions corresponding to the respective portions 301, 303, and 304 of the support member 300 by connecting the band bodies 410, 420, and 430 to each other.

The support member 300 has the line-symmetrical shape with respect to the center line A1 of the first band body 410 in the main body 110 (see FIGS. 5 and 11). Therefore, the hemostatic device 10 can uniformly apply forces along directions bilaterally symmetrical with respect to the support member 300 by wrapping the respective band bodies 420 and 430 extending from the main body 110 in directions bilaterally symmetrical with respect to the center line A1 of the first band body 410 around the right hand H1 of the patient.

As a result, the hemostatic device 10 can prevent the support member 300 from being displaced in the state where the support member 300 is disposed on the right hand H1 of the patient.

An inclined part exists in each portion (for example, the vicinity of the snuff box Sb) of the right hand H1 of the patient (see FIG. 16). Furthermore, a shape of the inclined part of the right hand H1 depends on an individual difference of the patient. For example, in a case where the inner surface of the support member is formed in a flat shape, it is difficult to dispose the support member along the inclined part of the right hand H1. In the hemostatic device 10, the inner surface 300*a* of the support member 300 is curved in the shape projecting in the direction away from the inflatable member 210 (see FIGS. 7 and 21). Therefore, the inner surface 300*a* of the support member 300 can be disposed along the right hand H1 of the patient by disposing the inner surface 300*a* of the support member 300 so as to overlap the inclined part of the right hand H1 of the patient. As a result, the hemostatic device 10 can dispose the support member 300 to overlap the first puncture site p1 without depending on a dominant hand of the patient or the way of placement by the operator. Therefore, in the hemostatic device 10, the support member 300 can be appropriately disposed at a desired position near the first puncture site p1.

In addition to the above-described points, since the inner surface 300*a* of the support member 300 is disposed along the body surface of the right hand H1 when the operator wraps the second band body 420 and the third band body 430 along the right hand H1 of the patient, the hemostatic device 10 can be disposed such that the band bodies 420 and 430 respectively extending from the side surface portions 303 and 304 of the support member 300 are close to or in close contact with the body surface of the right hand H1 of the patient (see FIG. 21). Therefore, the hemostatic device 10 can enhance the force of securing the support member 300 and the inflatable member 210 with respect to the right hand H1 of the patient. As a result, it is possible to prevent the support member 300 and the inflatable member 210 from being displaced even when an impact or the like is applied from the outside in the state where the hemostatic device 10 is worn on the right hand H1 of the patient.

The operator inflates the inflatable member 210 by injecting air into the inflatable member 210 in a state where the syringe is connected to the injection portion 281. As illustrated in FIGS. 20 and 21, in the hemostatic device 10, when the inflatable member 210 inflates, the inflatable member 210 applies a compressive force to the first puncture site p1.

The support member 300 made of a material harder than the inflatable member 210 presses the inflatable member 210 against the right hand H1 of the patient if the inflatable member 210 inflates in the state where the hemostatic device 10 is worn on the right hand H1 of the patient. As a result, the hemostatic device 10 can prevent the inflatable member 210 from floating from the right hand H1 of the patient. That is, the inflatable member 210 is prevented from lifting off of or shifting on the right hand H1 of the patient.

When performing hemostasis using the hemostatic device, the operator can strongly tighten the first band body disposed in the interdigital part fb, for example, in order to enhance the force of securing the support member with respect to the right hand H1 of the patient. The operator can firmly secure the support member to the right hand H1 of the patient by strongly tightening the first band body even if the support member is disposed in an unstable state on the right hand H1 of the patient. However, the patient sometimes feels pain when the first band body is strongly tightened. Therefore, in a case where the first band body cannot be strongly tightened due to the pain felt by the patient or the like, the hemostatic device may be disposed such that the inner surface of the support member is inclined with respect to the body surface of the right hand H1 of the patient. Specifically, the upper end of the support member on which the first band body is disposed floats to a position excessively away from the body surface of the right hand H1 of the patient as compared with the lower end located opposite to the upper end. As a result, in the hemostatic device, the support member is disposed to be inclined such that a distance between the inner surface of the support member and the body surface of the right hand H1 of the patient gradually decreases from the upper end to the lower end of the support member.

The hemostatic device 10 is configured such that the thickness t1 of each of the side surface portions 303 and 304 of the support member 300 becomes thinner from the upper end 301 to the lower end 302. In addition, the first band body 410 configured to be disposed in the interdigital part fb located between the fingers of the patient extends from the upper end 301 side of the support member 300, and is configured to press the upper end 301 side of the support member 300 against the right hand H1 of the patient. In the hemostatic device 10 configured as described above, when the inflatable member 210 starts to inflate in a state where the support member 300 and the inflatable member 210 are secured to the right hand H1 of the patient, the inflatable member 210 applies a force to the vicinity of the upper end 301 of the support member 300. The upper end 301 side of the support member 300 is lifted by the force applied by the inflatable member 210. As a result, the support member 300 is disposed such that the inner surface 300*a* of the support member 300 is substantially parallel with the body surface of the right hand H1 of the patient in a state where the inflatable member 210 inflates as illustrated in FIG. 20. Therefore, the hemostatic device 10 can apply a compressive force in a direction perpendicular to the first puncture site p1 when the inflatable member 210 inflates.

The inner surface 300*a* of the support member 300 is curved toward the second band body 420 side and the third band body 430 side (see FIGS. 7 and 21). As illustrated in FIG. 21, the hemostatic device 10 is disposed such that the inner surface 300*a* of the support member 300 is along the body surface of the right hand H1 of the patient in the state where the inflatable member 210 inflates. When the inflatable member 210 inflates, the hemostatic device 10 presses the inflatable member 210 along the body surface of the right hand H1 of the patient by the inner surface 300*a* of the support member 300. As a result, when the inflatable member 210 inflates, the inflatable member 210 applies a compressive force in a direction toward the first puncture site p1 from a center side in the width direction of the inner surface 300*a* of the support member 300 and the side surface portions 303 and 304 located at both ends in the width direction of the inner surface 300*a* of the support member 300. Therefore, the hemostatic device 10 can effectively enhance the compressive force applied to the first puncture site p1 by the inflatable member 210 as compared with a case where the inner surface 300*a* of the support member 300 is formed in a flat surface shape.

The support member 300 has a shape in which each of the corners 306*a*, 306*b*, 306*c*, and 306*d* is rounded (see FIG. 11). Therefore, the hemostatic device 10 can prevent each of the corners 306*a*, 306*b*, 306*c*, and 306*d* of the support member 300 from biting into the body surface of the right hand H1 of the patient while the inflatable member 210 inflates to apply the compressive force to the first puncture site p1.

After the inflatable member 210 inflates, the operator removes the sheath tube 610 of the introducer 600 from the first puncture site p1 as illustrated in FIG. 19. The operator confirms that there is no bleeding from the first puncture site p1 while bleeding is stopped using the hemostatic device 10. In a case where there is bleeding from the first puncture site p1, the operator can adjust an injection amount of air into the inflatable member 210.

According to the above process, the operator can stop bleeding at the first puncture site p1 formed on the right hand H1 of the patient using the hemostatic device 10.

Each of the support member 300 and the inflatable member 210 included in the hemostatic device 10 has the line-symmetrical shape with respect to the center line A1 of the first band body 410 in the main body 110. Therefore, in the case of being used to stop bleeding at a puncture site formed at a position corresponding to the first puncture site p1 in the left hand of the patient and a puncture site formed at a position corresponding to the second puncture site p2 in the left hand of the patient, the hemostatic device 10 can also exhibit the same effects as those in the case of being used to stop bleeding at the first puncture site p1 (or the second puncture site p2) of the right hand H1 described above.

As described above, the hemostatic device 10 according to the present embodiment includes the cover member 100 configured to cover the first puncture site p1 and the inflatable member 210 (pressing member 200) disposed on the cover member 100 and configured to compress the first puncture site p1. The cover member 100 includes the main body 110 in which the inflatable member 210 is located, the first band body 410 configured to be disposed between the fingers of the patient and extends from the main body 110 in the first direction, the second band body 420 extending from the main body 110 in the second direction different from the first direction, and the third band body 430 facing the second band body 420 across the inflatable member 210 and extending from the main body 110 in a different direction from the first band body 410 and the second band body 420.

The main body 110 includes the support member 300 disposed so as to overlap the inflatable member 210 and made of a material harder than the inflatable member 210. The main body 110 includes the first region 111 where the support member 300 is located, and the second region 112 located between the first region 111 and each of the first band body 410, the second band body 420, and the third band body 430. The second region 112 is made of a material having higher ductility than the support member 300. The width wm2 of the second region 112*b* located between the first region 111 and the second band body 420 and the width wm3 of the second region 112*c* located between the first region 111 and the third band body 430 decrease from the distal side of the support member 300 to the proximal side of the support member 300.

The main body 110 of the hemostatic device 10 configured as described above includes the support member 300 disposed so as to overlap the inflatable member 210 and made of the material harder than the inflatable member 210. Furthermore, the main body 110 includes the first region 111 where the support member 300 is located, and the second region 112 located between the first region 111 and each of the first band body 410, the second band body 420, and the third band body 430. The second region 112 is made of a material having higher ductility than the support member 300. Therefore, the second region 112 is configured to move in accordance with the pulling operation when each of the band bodies 410, 420, and 430 is pulled. It is possible to appropriately adjust the position where each of the band bodies 410, 420, and 430 is wrapped around the right hand H1 of the patient by pulling each of the band bodies 410, 420, and 430 to move the second region 112 in the hemostatic device 10 at the time of causing the hemostatic device 10 to be worn on the right hand H1 of the patient. Therefore, the hemostatic device 10 can be applied to various patients having different sizes and shapes of the right hand H1, and can also be applied to hemostasis of the first puncture sites p1 formed at different positions. Further, in the hemostatic device 10, the width wm2 of the second region 112*b* located between the first region 111 and the second band body 420 and the width wm3 of the second region 112*c* located between the first region 111 and the third band body 430 decrease (narrow) from the distal side of the support member 300 to the proximal side of the support member 300. Therefore, the hemostatic device 10 can prevent the second regions 112*b* and 112*c* located on the proximal side of the support member 300 from being excessively moved when the second band body 420 and the third band body 430 are wrapped around the right hand H1 of the patient. Therefore, when the second band body 420 and the third band body 430 of the hemostatic device 10 are wrapped around the right hand H1 of the patient, positions where the second band body 420 and the third band body 430 are wrapped around the right hand H1 of the patient can be prevented from being shifted to the proximal side of the support member 300. In the hemostatic device 10, the second band body 420 and the third band body 430 can be wrapped around the right hand H1 of the patient along directions of being separated from each other with the support member 300 as a reference, the directions being substantially horizontal to each other. Therefore, the hemostatic device 10 enables the second band body 420 and the third band body 430 to be more firmly wrapped around the right hand H1 of the patient. Therefore, the hemostatic device 10 can improve the compressive force applied to the first puncture site p1 by the inflatable member 210 in the state where the hemostatic device 10 is worn on the right hand H1 of the patient.

In the hemostatic device 10, the width wm1 of the second region 112*a* located between the first region 111 and the first band body 410 is smaller than the width wm2 of the second region 112*b* located between the first region 111 and the second band body 420 and the width wm3 of the second region 112*c* located between the first region 111 and the third band body 430.

As described above, the width wm1 of the second region 112*a* is smaller than the width wm2 of the second region 112*b* and the width wm3 of the second region 112*c* in the hemostatic device 10. Therefore, the second region 112*a* has a narrower movable range as compared with the other second regions 112*b* and 112*c*. Therefore, the hemostatic device 10 can suppress the second region 112*a* located between the first region 111 and the first band body 410 from being excessively extended when the first band body 410 is wrapped along the interdigital part fb. As a result, the hemostatic device 10 can secure the first band body 410 in a state of being firmly tightened to the interdigital part fb.

The second region 112 is located around the first region 111, and the edge portion of the main body 110 located between each two of the first band body 410, the second band body 420, and the third band body 430 is formed of the second region 112.

As described above, in the hemostatic device 10, the second region 112 is located around the first region 111, and the second region 112 is located between each two of the band bodies 410, 420, and 430. Therefore, the edge portion of the main body 110 connecting each of the band bodies 410, 420, and 430 is formed of the second region 112. Therefore, the hemostatic device 10 has a structure in which mobility is given between each two of the band bodies 410, 420, and 430 by the second region 112 located between each two of the band bodies 410, 420, and 430. Therefore, in the hemostatic device 10, the mobility of each of the band bodies 410, 420, and 430 is further improved, and the convenience is further improved.

The support member 300 includes the upper end 301 that is located on the first band body 410 side and forms an end of the support member 300 and the lower end 302 forming an end opposite to the upper end 301. The width of the support member 300 decreases from the upper end 301 to the lower end 302.

As described above, the width of the support member 300 decreases from the upper end 301 to the lower end 302 in the hemostatic device 10. Therefore, the hemostatic device 10 can be configured such that the widths wm2 and wm3 of the second regions 112*b* and 112*c* decrease from the upper end 301 side to the lower end 302 side of the support member 300, and the widths wm2 and wm3 of the second regions 112*b* and 112*c* located near the lower end 302 of the support member 300 can be prevented from being formed to be excessively small. As a result, when the second band body 420 and the third band body 430 are wrapped around the right hand H1 of the patient, the hemostatic device 10 can suppress the band bodies 420 and 430 from interfering with the support member 300 in the vicinity of the lower end 302 of the support member 300 while maintaining the mobility in the second regions 112*b* and 112*c* near the lower end 302 of the support member 300.

The support member 300 has the side surface portions 303 and 304 connecting the upper end 301 and the lower end 302. Each of the side surface portions 303 and 304 forms the first angle θ1 with respect to the center line A1 of the first band body 410 in a plan view. The first angle θ1 is smaller the second angle θ2 formed by the straight line VL3 orthogonal to the center line A2 of the second band body 420 and the center line A1 of the first band body 410 and the third angle θ3 formed by the straight line VL4 orthogonal to the center line A3 of the third band body 430 and the center line A1 of the first band body 410.

As described above, in the hemostatic device 10, the first angle θ1 formed by each of the side surface portions 303 and 304 of the support member 300 and the center line A1 of the first band body 410 is smaller than the second angle θ2 formed by the straight line VL3 orthogonal to the center line A2 of the second band body 420 and the center line A1 of the first band body 410, and is smaller than the third angle θ3 formed by the straight line VL4 orthogonal to the center line A3 of the third band body 430 and the center line A1 of the first band body 410. Therefore, the hemostatic device 10 can be configured such that each of the widths wm2 and wm3 gradually decreases from the distal side to the proximal side (from the upper end 301 side to the lower end 302 side) of the support member 300 according to a difference in angle between the first angle θ1 and each corresponding one of the angles θ2 and θ3. As a result, when the second band body 420 and the third band body 430 are wrapped around the right hand H1 of the patient, the hemostatic device 10 can more reliably suppress the band bodies 420 and 430 from interfering with the support member 300 in the vicinity of the lower end 302 of the support member 300 while maintaining the mobility in the second regions 112*b* and 112*c* near the lower end 302 of the support member 300.

Each of the first band body 410, the second band body 420, and the third band body 430 is made of the material having higher flexibility than the support member 300 and having lower ductility than the material of the second region 112, and is fixed secured to the main body 110 on the inner surface 110*a* side of the main body 110.

As described above, each of the band bodies 410, 420, and 430 can be made of the material having higher flexibility than the support member 300 in the hemostatic device 10. Furthermore, in the hemostatic device 10, each of the band bodies 410, 420, and 430 is secured to the main body 110 on the inner surface 110*a* side of the main body 110. Therefore, the hemostatic device 10 is disposed such that the one ends 411, 421, and 431 of the band bodies 410, 420, and 430 come into contact with the body surface of the right hand H1 in the state where the hemostatic device 10 is worn on the right hand H1 of the patient, and the main body 110 is disposed to overlap thereon. Therefore, since the hemostatic device 10 is disposed such that each of the band bodies 410, 420, and 430 configured to be more flexible comes into contact with the body surface, it is possible to prevent the patient from feeling pain or the like when the vicinity of the region where the main body 110 is connected to each of the band bodies 410, 420, and 430 comes into contact with the body surface of the patient. Furthermore, the second region 112 of the main body 110 is made of the material having higher ductility than each of the band bodies 410, 420, and 430 in the hemostatic device 10. Therefore, the hemostatic device 10 is configured such that the second region 112 has appropriate mobility.

In the first band body 410, the second band body 420, and the third band body 430, the ends 411*a*, 421*a*, and 431*a* of the side surfaces located on both sides in the width direction of the first band body 410, the second band body 420, and the third band body 430 are not secured to the main body 110.

Since the ends 411*a*, 421*a*, and 431*a* located on the side surfaces of the band bodies 410, 420, and 430 in the width direction are not secured to the main body 110 as described above, the fused portions 141, 142, and 143 can be prevented from coming into contact with the body surface when the patient moves to twist the wrist toward the dorsal side of the right hand H1 or the like in the state where the hemostatic device 10 is worn on the right hand H1 of the patient. Therefore, the hemostatic device 10 can prevent the patient from feeling pain or discomfort when the hemostatic device 10 is worn on the right hand H1 of the patient.

Next, modifications of the above-described embodiment will be described. In the description of the modifications, a detailed description regarding the features, members and the process of using the hemostatic device already described in the above-described embodiment will not be repeated. Furthermore, features and aspects that are not particularly described in the modifications can be the same as those in the above-described embodiment.

Each of FIGS. 25 to 28 illustrates a part of a hemostatic device according to each of the modifications in an enlarged manner. FIGS. 25 to 28 are views corresponding to the plan view of FIG. 9 used in the description of the hemostatic device 10 according to the above-described embodiment. The illustration of some constituent members such as the inflatable member 210 is omitted in FIGS. 25 to 28 as in FIG. 9.

First Modification

Figure 25:
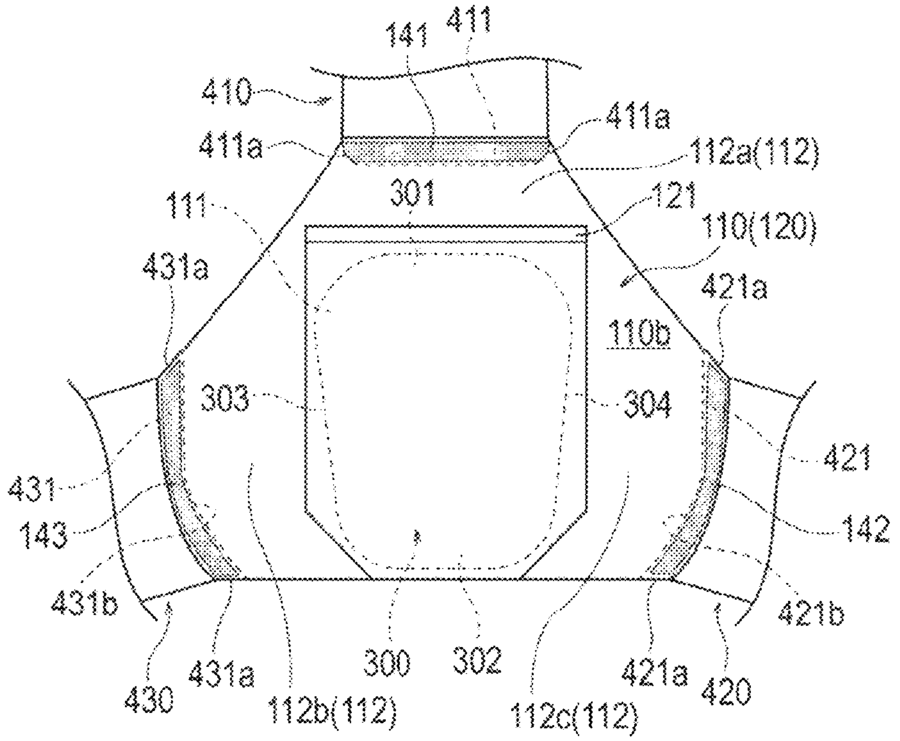
FIG. 25 is a view briefly illustrating a part of a hemostatic device according to a first modification.

FIG. 25 illustrates a hemostatic device according to a first modification.

The hemostatic device according to the first modification is different from that of the above-described embodiment in terms of configurations of the second band body 420 and the third band body 430.

As illustrated in FIG. 25, the one end 421 of the second band body 420 located on the main body 110 side has a first concave portion 421*b* curved toward the other end 422 side (see FIG. 1) located on a side opposite to the main body 110 of the second band body 420 in a plan view. In other words, the first concave portion 421*b* faces toward the third band body 430.

As illustrated in FIG. 25, the one end 431 of the third band body 430 located on the main body 110 side has a second concave portion 431*b* curved toward the other end 432 side (see FIG. 1) located on a side opposite to the main body 110 of the third band body 430 in the plan view. In other words, the second concave portion 431*b* faces toward the second band body 420.

The second band body 420 and the third band body 430 are connected to the main body 110 at the one ends 421 and 431, respectively.

A method of connecting the main body 110 and each of the band bodies 420 and 430 is, for example, fusion bonding. The fused portions 142 and 143 are formed in the concave portions 421*b* and 431*b*, respectively. In other words, the fusion bonded regions have the illustrated curved shape.

In the hemostatic device according to the first modification, the concave portions 421*b* and 431*b* are formed in the one ends 421 and 431 of the band bodies 420 and 430, respectively. Therefore, the hemostatic device according to the first modification can widen a width of each of the second regions 112*b* and 112*c* around the first region 111 as compared with the hemostatic device 10 in which the one ends 421 and 431 of the band bodies 420 and 430 are linearly formed. Therefore, when the main body 110 is made of a transparent material in the hemostatic device according to the first modification, the area of each of the second regions 112*b* and 112*c* functioning as window portions increases. Therefore, the hemostatic device according to the first modification allows an operator to visually confirm the marker portion 260 and/or the first puncture site p1 more easily in a state where the hemostatic device is worn on the right hand H1 of a patient.

Second Modification

Figure 26:
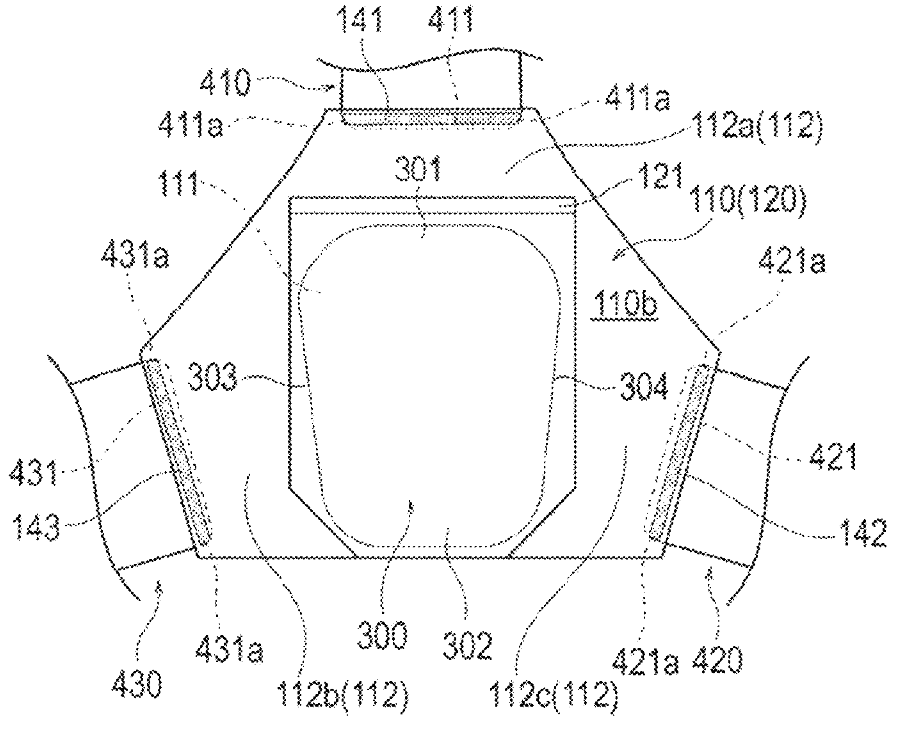
FIG. 26 is a view briefly illustrating a part of a hemostatic device according to a second modification.

FIG. 26 illustrates a hemostatic device according to a second modification.

As illustrated in FIG. 26, for example, a width of each of the one ends 411, 421, and 431 of the band bodies 410, 420, and 430 can be formed to be smaller than a width of a part of the main body 110 to which each of the one ends 411, 421, and 431 is connected.

In a case where each of the band bodies 410, 420, and 430 is configured as described above, when a patient wearing the hemostatic device 10 moves to twist the wrist or the like (see FIG. 22), the main body 110 is likely to come into contact with a body surface of the patient, and the fused portions 141, 142, and 143 located at the one ends 411, 421, and 431 are less likely to come into contact with the body surface of the patient. Therefore, it is possible to effectively prevent the patient from feeling pain or the like when the patient moves to twist the wrist or the like. The fused portions 141, 142, and 143 are less likely to come into contact with the body surface of the patient when the patient moves to twist the wrist or the like as described above. Therefore, for example, as illustrated in FIG. 26, the fused portions 141, 142, and 143 can be formed so as to extend to the ends 411*a*, 421*a*, and 431*a*, respectively.

Third Modification

Figure 27:
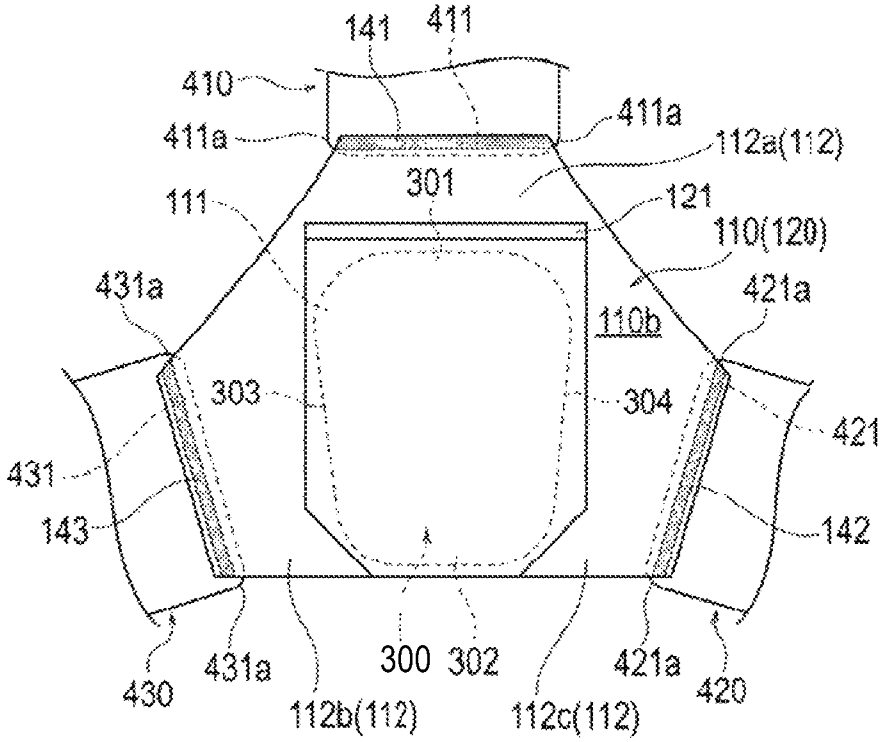
FIG. 27 is a view briefly illustrating a part of a hemostatic device according to a third modification.

FIG. 27 illustrates a hemostatic device according to a third modification.

As illustrated in FIG. 27, for example, a width of each of the one ends 411, 421, and 431 of the band bodies 410, 420, and 430 can be formed to be larger than a width of a part of the main body 110 to which each of the one ends 411, 421, and 431 is connected.

In a case where each of the band bodies 410, 420, and 430 is configured as described above, when a patient wearing the hemostatic device 10 moves to twist the wrist or the like (see FIG. 22), the ends 411*a*, 421*a*, and 431*a* of the band bodies 410, 420, and 430 are likely to come into contact with a body surface of the patient, and the fused portions 141, 142, and 143 located at the one ends 411, 421, and 431 are less likely to come into contact with the body surface of the patient. Therefore, it is possible to effectively prevent the patient from feeling pain or the like when the patient moves to twist the wrist or the like. The fused portions 141, 142, and 143 are less likely to come into contact with the body surface of the patient when the patient moves to twist the wrist or the like as described above. Therefore, for example, as illustrated in FIG. 27, the fused portions 141, 142, and 143 can be formed in the entire range overlapping the one ends 411, 421, and 431, respectively, in the main body 110.

Fourth Modification

Figure 28:
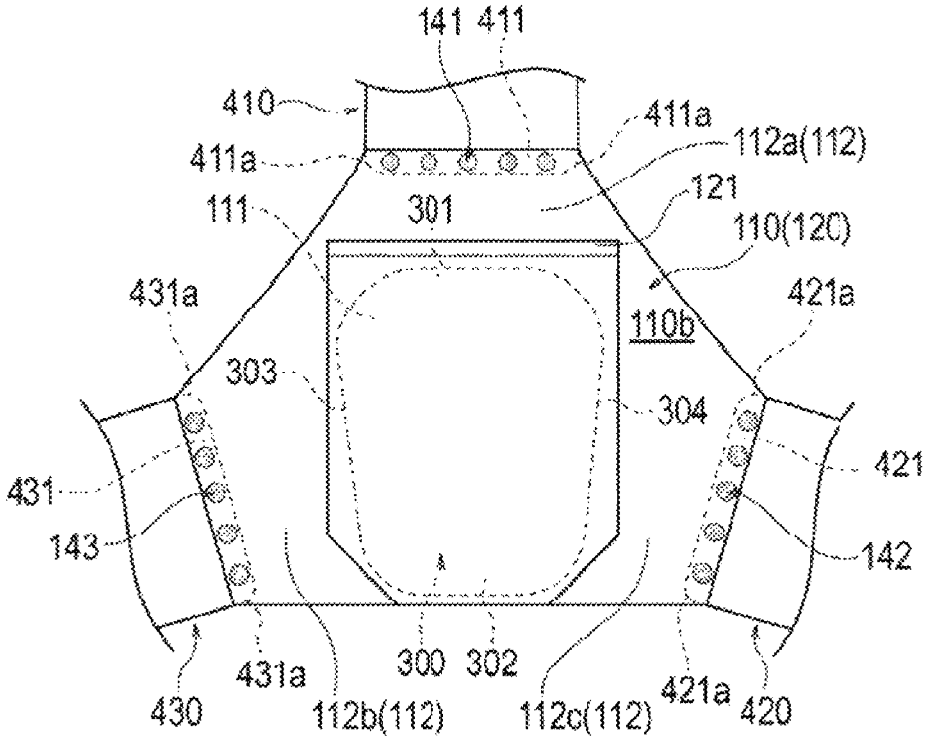
FIG. 28 is a view briefly illustrating a part of a hemostatic device according to a fourth modification.

FIG. 28 illustrates a hemostatic device according to a fourth modification.

As illustrated in FIG. 28, for example, the fused portions 141, 142, and 143 may be configured as a plurality of point-shaped fused portions disposed at intervals from each other in a plan view. That is, the immediately adjacent fused portions 141, 142, 143 are spaced apart from one another, and unfused portions exist between the fused portions. When the fused portions 141, 142, and 143 are configured in this manner, it is possible to reduce the area where the fused portions 141, 142, and 143 are formed at the one ends 411, 421, and 431, respectively. Therefore, the hemostatic device according to the fourth modification can reduce the area of a part that becomes hard in each of the one ends 411, 421, and 431, and can effectively prevent a patient wearing the hemostatic device from feeling pain or the like.

A formation pattern (shapes and the number) of the fused portions is not particularly limited as long as it is possible to secure a securing force of securing each of the band bodies 410, 420, and 430 to the main body 110. For example, the fused portion can be formed of a broken line pattern, a pattern extending in an oblique direction, a lattice pattern, a pattern extending in a direction orthogonal to a width direction of the band body, or the like.

Although the new hemostatic device disclosed here has been described above through the embodiment and the modifications, the present invention is not limited only to the content described in the specification and can be appropriately changed.

The shape, size, and the like of each part of the hemostatic device are not particularly limited as long as a puncture site can be compressed to stop bleeding by the pressing member disposed at the puncture site, and can be appropriately changed.

Specific shapes (planar shape and cross-sectional shape) of the inflatable member and the support member are not limited to the shapes illustrated in the embodiment.

The method of connecting each band body and the main body is not limited to fusion bonding. As the method of connecting each band body and the main body, for example, adhesion by an adhesive, connection by a mechanical structure such as a rivet pin or a fastener, and the like can be arbitrarily selected according to a desired securing force.

A configuration of the pressing member that applies a compressive force to the puncture site is not limited to the inflatable member (balloon). The pressing member can also be configured using, for example, a resin material such as plastic configured to be capable of applying the compressive force to the puncture site, a member made of gel or the like, an elastic material such as a sponge-like substance, an assembly of fibers such as cotton, metal, a member having a predetermined three-dimensional shape (a sphere, an ellipsoid, a triangular pyramid, or the like), or one obtained by combining these as appropriate.

The hemostatic device can also be configured for the purpose of hemostasis other than the puncture site formed on the hand. For example, the hemostatic device can also be applied to hemostasis of a puncture site formed on an arm, a leg, or the like of a patient using the pressing member of the embodiment.

The detailed description above describes embodiments/modifications of a hemostatic device and method of use representing examples of the new hemostatic device and method of use disclosed here. The invention is not limited, however, to the precise embodiments. modifications and variations described. Various changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims

What is claimed is:

1. A hemostatic device comprising:
- a cover member configured to cover a puncture site on a patient;
- a pressing member disposed on the cover member and configured to compress the puncture site;
- the cover member including a main body in which the pressing member is located, a first band body configured to be disposed between fingers of the patient and extending from the main body in a first direction, a second band body extending from the main body in a second direction different from the first direction, and a third band body facing the second band body across the pressing member and extending from the main body in a different direction from the first band body and the second band body;
- the main body including a support member overlapping the pressing member and made of a material harder than the pressing member;
- the main body having a first region where the support member is located, and a second region located between the first region and each of the first band body, the second band body, and the third band body;
- the support member having an upper end that is located on a side where the first band body is disposed and forming an end of the support member and a lower end forming an end opposite to the upper end;
- a width of the support member decreasing from the upper end of the support member to the lower end of the support member:
- the second region is made of a material having higher ductility than the support member; and
- a width of the second region located between the first region and the second band body and a width of the second region located between the first region and the third band body decreasing from a distal side of the support member to a proximal side of the support member.

2. The hemostatic device according to claim 1, wherein a width of the second region located between the first region and the first band body is smaller than the width of the second region located between the first region and the second band body and is smaller than the width of the second region located between the first region and the third band body.

3. The hemostatic device according to claim 1, wherein the second region is located around the first region, and an edge portion of the main body located between each two of the first band body, the second band body, and the third band body constitutes part of the second region.

4. The hemostatic device according to claim 1, wherein
- the support member has a side surface portion connecting the upper end and the lower end,
- the side surface portion forms a first angle with respect to a center line of the first band body in a plan view, the first angle being other than zero degrees, and
- the first angle is smaller than a second angle and a third angle, the second angle being formed by a straight line orthogonal to a center line of the second band body and the center line of the first band body, the third angle being formed by a straight line orthogonal to a center line of the third band body and the center line of the first band body.

5. The hemostatic device according to claim 1, wherein the first band body, the second band body, and the third band body are made of a material that has higher flexibility than the support member and has lower ductility than the material of the second region, and are secured to the main body on an inner surface side of the main body, the pressing member being located on the inner surface side of the main body.

6. The hemostatic device according to claim 1, wherein in the first band body, the second band body, and the third band body, ends of side surfaces located on both sides in a width direction of the first band body, the second band body, and the third band body are not secured to the main body.

7. The hemostatic device according to claim 1, wherein
- an end of the second band body located on a side where the main body is disposed has a first concave portion curved toward an end of the second band body located on a side opposite to the main body in a plan view, an end of the third band body located on a side where the main body is disposed has a second concave portion curved toward an end of the third band body located on a side opposite to the main body in the plan view, and the second band body and the third band body are connected to the main body in the first concave portion and the second concave portion.

8. A hemostatic device to be applied to a hand of a patient to stop bleeding at a puncture site on the patient's hand, the hemostatic device comprising:

a pressing member configured to compress the puncture site on the hand of the patient;

a cover member configured to cover the puncture site on the patient's hand and positioned in overlying relation to the pressing member;

the cover member including a main body, a first band body configured to be disposed between fingers of the patient's hand, a second band body and a third band body, the second and third band bodies being configured to be wrapped around the hand of the patient so that fasteners provided on the second and third band bodies engage one another to secure the second and third band bodies to each other in a wrapped state around the patient's hand;

the main body having an outer periphery and including a support member, a first layer and a second layer, the first layer having an outer periphery, the support member also having an outer periphery, the support member being located between the first and second layers and overlying the pressing member, the support member being made of a material different from the first and second layers, the support member being harder than the pressing member, the support member including one side and an oppositely facing other side;

the first band body extending from the main body in a first direction, the second band body extending from the main body in a second direction different from the first direction, and the third band body extending from the main body in a third direction different from both the first direction and the second direction;

the second band body having a center line and an end portion terminating at a free end, the third band body having a center line and an end portion terminating at a free end, the center line of the second band body and the center line of the third band body intersecting one another in the support member as seen in a plan view of the hemostatic device;

the outer periphery of the main body being located outwardly of the outer periphery of the first layer and the outer periphery of the support member in the plan view;

the end portion of the second band body being fixed to the outer periphery of the main body so that the free end of the second band body faces the one side of the support member in the plan view, a distance between the free end of the second band body and the one side of the support member in the plan view decreasing in a direction away from the first band body; and the end portion of the third band body being fixed to the outer periphery of the main body so that the free end of the third band body faces the other side of the support member in the plan view, a distance between the free end of the third band body and the other side of the support member in the plan view decreasing in a direction away from the first band body.

9. The hemostatic device according to claim 8, wherein the outer periphery of the main body to which the second band body and the third band body are fixed is an outer periphery of the second layer.

10. The hemostatic device according to claim 8, wherein the support member has a curved shape, with a concave shape facing towards the pressing member and a convex shape facing away from the pressing member.

11. The hemostatic device according to claim 8, wherein the support member has one end and an opposite end, the one end of the support member being located closer to the first band body than the opposite end of the support member, the support member having a width defined by a distance between the one side of the support member and the other side of the support body, the width of the support member decreasing in a direction from the one end of the support member towards the opposite end of the support member.

12. The hemostatic device according to claim 8, wherein the support member has one end and an opposite end, the one end of the support member being located closer to the first band body than the opposite end of the support member, the one side and the other side of the support member decreasing in thickness in a direction from the one end of the support member towards the opposite end of the support member.

13. The hemostatic device according to claim 8, wherein the first band body has a center line, the one side of the support member extending along a line that forms an angle other than zero degrees with the center line of the first band body in the plan view, the other side of the support member extending along a line that forms an angle other than zero degrees with the center line of the first band body.

14. The hemostatic device according to claim 8, wherein the first band body has a center line, the one side of the support member and the other side of the support member extending along respective lines that each form a first angle other than zero degrees with the center line of the first band body in plan view, the first angle being less than a second angle and less than a third angle, the second angle being formed by a straight line orthogonal to the center line of the second band body and the center line of the first band body, the third angle being formed by a straight line orthogonal to a center line of the third band body and the center line of the first band body.

15. A hemostatic device to be applied to a hand of a patient to stop bleeding at a puncture site on the patient's hand, the hemostatic device comprising:

a pressing member configured to compress the puncture site on the hand of the patient;

a cover member configured to cover the puncture site on the patient's hand and positioned in overlying relation to the pressing member;

the cover member including a main body, a first band body configured to be disposed between fingers of the patient's hand, a second band body and a third band body, the second and third band bodies being configured to be wrapped around the hand of the patient so that fasteners provided on the second and third band bodies engage one another to secure the second and third band bodies to each other in a wrapped state around the patient's hand;

the main body including a support member overlapping the pressing member and made of a material harder than the pressing member, the main body also including sheet material overlying the support member, the sheet material having an outer periphery;

the first band body having a center line and an end, the second band body having a center line and an end, the third band body having a center line and an end, the center line of the first band body intersecting the support member as seen in a plan view of the hemostatic device, the center line of the second band body and the center line of the third band body intersecting one another in the support member as seen in the plan view of the hemostatic device;

the end of the first band body being fixed to the outer periphery of the sheet material of the main body so that the end of the first band body and a first portion of the outer periphery of the sheet material are positioned in overlying relation to each other, the end of the second band body being fixed to the outer periphery of the sheet material of the main body so that the end of the second band body and a second portion of the outer periphery of the sheet material are positioned in overlying relation to each other, the end of the third band body being fixed to the outer periphery of the sheet material of the main body so that the end of the third band body and a third portion of the outer periphery of the sheet material are positioned in overlying relation to each other;

the second portion of the outer periphery of the sheet material and the third portion of the outer periphery of the sheet material being spaced outwardly away from an outer periphery of the support member as seen in the plan view; and i) the end of the second band body and the end of the third band body having a concavely curved end surface facing toward the support member; or ii) the end of the second band body that is positioned in overlying relation to the second portion of the outer periphery of the sheet material having a width less than a width of the second portion of the outer periphery of the sheet material, and the end of the third band body that is positioned in overlying relation to the third portion of the outer periphery of the sheet material having a width less than a width of the third portion of the outer periphery of the sheet material; or iii) the end of the second band body that is positioned in overlying relation to the second portion of the outer periphery of the sheet material having a width greater than a width of the second portion of the outer periphery of the sheet material, and the end of the third band body that is positioned in overlying relation to the third portion of the outer periphery of the sheet material having a width greater than a width of the third portion of the outer periphery of the sheet material; or iv) the end of the second band body being fused to the outer periphery of the sheet material of the main body at a plurality of second band body fused portions that are spaced apart from one another so that an unfused portion exists between immediately adjacent second band body fused portions, and the end of the third band body being fused to the outer periphery of the sheet material of the main body at a plurality of third band body fused portions that are spaced apart from one another so that an unfused portion exists between immediately adjacent third band body fused portions.

16. The hemostatic device according to claim 15, wherein the end of the second band body and the end of the third band body each have the concavely curved end surface facing toward the support member, the end of the second band body being fused to the outer periphery of the sheet material of the main body at a second band body fused portion that is concavely curved so that a concave surface of the second band body fused portion faces towards the support member, the end of the third band body being fused to the outer periphery of the sheet material of the main body at a third band body fused portion that is concavely curved so that a concave surface of the third band body fused portion faces towards the support member.

17. The hemostatic device according to claim 15, wherein the end of the second band body that is positioned in overlying relation to the second portion of the outer periphery of the sheet material has the width less than the width of the second portion of the outer periphery of the sheet material, and the end of the third band body that is positioned in overlying relation to the third portion of the outer periphery of the sheet material has the width less than the width of the third portion of the outer periphery of the sheet material, and the end of the first band body that is positioned in overlying relation to the first portion of the outer periphery of the sheet material having a width less than a width of the first portion of the outer periphery of the sheet material.

18. The hemostatic device according to claim 15, wherein the end of the second band body that is positioned in overlying relation to the second portion of the outer periphery of the sheet material has the width greater than the width of the second portion of the outer periphery of the sheet material, and the end of the third band body that is positioned in overlying relation to the third portion of the outer periphery of the sheet material has the width greater than the width of the third portion of the outer periphery of the sheet material, the end of the first band body that is positioned in overlying relation to the first portion of the outer periphery of the sheet material having a width greater than a width of the first portion of the outer periphery of the sheet material.

19. The hemostatic device according to claim 15, wherein the end of the second band body is fused to the outer periphery of the sheet material of the main body at the plurality of second band body fused portions and the end of the third band body is fused to the outer periphery of the sheet material of the main body at the plurality of third band body fused portions, the end of the first band body being fused to the outer periphery of the sheet material of the main body at a plurality of first band body fused portions that are spaced apart from one another so that an unfused portion exists between immediately adjacent first band body fused portions.

* * * * *